(12) United States Patent
Ordway et al.

(10) Patent No.: US 8,420,315 B2
(45) Date of Patent: Apr. 16, 2013

(54) SINGLE NUCLEOTIDE POLYMORPHISMS AND COMBINATIONS OF NOVEL AND KNOWN POLYMORPHISMS FOR DETERMINING THE ALLELE-SPECIFIC EXPRESSION OF THE IGF2 GENE

(75) Inventors: Jared Ordway, St. Louis, MO (US); Nathan Lakey, Chesterfield, MO (US); Rebecca Maloney, Centreville, VA (US); Theresa Rohlfing, Webster Groves, MO (US)

(73) Assignee: Orion Genomics LLC, St. Louis, MO (US)

( * ) Notice: Subject to any disclaimer, the term of this patent is extended or adjusted under 35 U.S.C. 154(b) by 227 days.

(21) Appl. No.: 12/672,066

(22) PCT Filed: Aug. 6, 2008

(86) PCT No.: PCT/US2008/072356
§ 371 (c)(1),
(2), (4) Date: May 19, 2010

(87) PCT Pub. No.: WO2009/021054
PCT Pub. Date: Feb. 12, 2009

(65) Prior Publication Data
US 2011/0311967 A1 Dec. 22, 2011

Related U.S. Application Data

(60) Provisional application No. 60/954,290, filed on Aug. 6, 2007, provisional application No. 60/988,715, filed on Nov. 16, 2007.

(51) Int. Cl.
*C12Q 1/68* (2006.01)
*C07H 21/02* (2006.01)

(52) U.S. Cl.
USPC .......................................... 435/6.1; 536/23.1

(58) Field of Classification Search ........................ None
See application file for complete search history.

(56) References Cited

U.S. PATENT DOCUMENTS

| | | | |
|---|---|---|---|
| 2001/0007749 A1 | 7/2001 | Feinberg | |
| 2003/0232353 A1 | 12/2003 | Kennedy et al. | |
| 2006/0292626 A1 | 12/2006 | Kenned | |
| 2008/0220983 A1 | 9/2008 | Trinklein et al. | |
| 2010/0286926 A1* | 11/2010 | Ordway et al. | 702/19 |

FOREIGN PATENT DOCUMENTS

| | | |
|---|---|---|
| WO | 95/11995 A1 | 5/1995 |
| WO | WO 00/04187 | 1/2000 |
| WO | WO 2004/003003 | 1/2004 |
| WO | 2009/021054 A2 | 2/2009 |

OTHER PUBLICATIONS

GenBank Locus DQ104205 (Apr. 19, 2006) *Homo sapiens* INSIGF long transcript variant mRNA, complete cds, alternatively spliced. from www.ncbi.nlm.nih.gov, pp. 1-3.*
Crowles C.R. et al. Nature Genetics (Nov. 2002) vol. 32, pp. 432-437.*
Wu M.-S. et al. Cancer Letters (1997) vol. 120, pp. 9-14.*
Reference SNP(refSNP) Cluster Report: rs2585, from www.ncbi.nlm.nih.gov. printed on Apr. 30, 2012, pp. 1-4.*
Reference SNP(refSNP) Cluster Report: rs7873, from www.ncbi.nlm.nih.gov. printed on Apr. 30, 2012, pp. 1-3.*
dbSNP Reference SNP (refSNP) Cluster Report: rs74050124, printed on Sep. 17, 2012 from www.ncbi.nlm.nih.gov, pp. 1-2.*
International Search Report dated Jan. 26, 2009 for related International Patent Application No. PCTUS2008/072356, filed Aug. 6, 2008.
Cui et al., "Loss of Imprinting in Normal Tissue of Colorectal Cancer Patients with Microsatellite Instability," 1998, Nature Medicine, vol. 4, No. 11, pp. 1276-1280.
Gaunt et al. "Positive associations between single nucleotide polymorphisms in the *IGF2* gene region and body mass index in adult males," 2001, Human Molecular Genetics, vol. 10, No. 14, pp. 1491-1501.
Uejima et al., "Hot-stop PCR: a simple and general assay for linear quantification of allele ratios," 2000, Nature Genetics, vol. 25, No. 4, 375-376.
Woodson et al, "Loss of Insulin-Like Growth Factor-II Imprinting and the Presence of Screen-Detected Colorectal Adenomas in Women," 2004, Journal of the National Cancer Institute, vol. 96, No. 5, pp. 407-410.
Yun et al., "Analysis of IGF2 gene imprinting in breast and colorectal cancer by allele specific-PCR," 1999, Journal of Pathology, vol. 187, pp. 518-522.
GenBank Accession No. AC132217.15; "*Homo sapiens* chromosome 11, clone RP11-889I17, complete sequence"; version GI:28460836; May 1, 2003.
Kurg et al.; "Arrayed Primer Extension: Solid-Phase Four-Color DNA Resequencing and Mutation Detection Technology"; *Genetic Testing;* 4:1-7 (Nov. 2000).
Murphy et al.; "Frequent *IGF2/H19* domain epigenetic alterations and elevated *IGF2* expression in epithelial ovarian cancer"; *Mol. Cancer Res.* 4(4):283-292 (2006) ePub Apr. 7, 2006.
O'Neill et al.; "Allelic expression of *IGF2* in marsupials and birds"; *Dev. Genes Evol.*; 210:18-20 (2000).
Prawitt et al.; "Microdeletion of target sites for insulator protein CTCF in a chromosome 11p15 imprinting center in Beckwith-Wiedmann syndrome and Wilms' tumor"; *Proc. Natl. Acad. Sci. USA;* 102(11):4085-4092 (Mar. 2005).
Office Action from U.S. Appl. No. 12/704,474, dated Apr. 5, 2012.
Barratt et al.; "Identification of the sources of error in allele frequency estimations from pooled DNA indicates an optimal experimental design"; *Ann. Hum. Genet.*; 66(5-6):393-405 (2002).
Bjornsson et al.; "Epigenetic Specificity of Loss of Imprinting of the IGF2 Gene in Wilms Tumors"; *J. Nat. Cancer Inst.;* 99(16):1270-1273 (2007).
Supplementary European Search Report from EP 10741738 dated Sep. 19, 2012.

* cited by examiner

*Primary Examiner* — Stephen Kapushoc
(74) *Attorney, Agent, or Firm* — Kilpatrick Townsend & Stockton LLP

(57) ABSTRACT

Single nucleotide polymorphisms and uses for determining the imprinting status of the Insulin Growth Factor-2 gene in a clinical specimen are described.

4 Claims, 10 Drawing Sheets

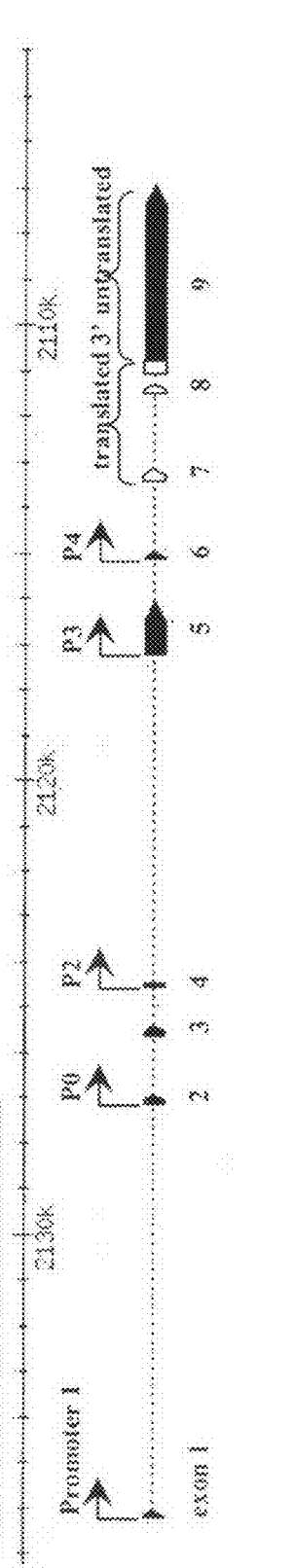
*Figure 1A    IGF2 Gene Model*
*Figure 1B    Linkage Blocks at IGF2 – HapMap Project*
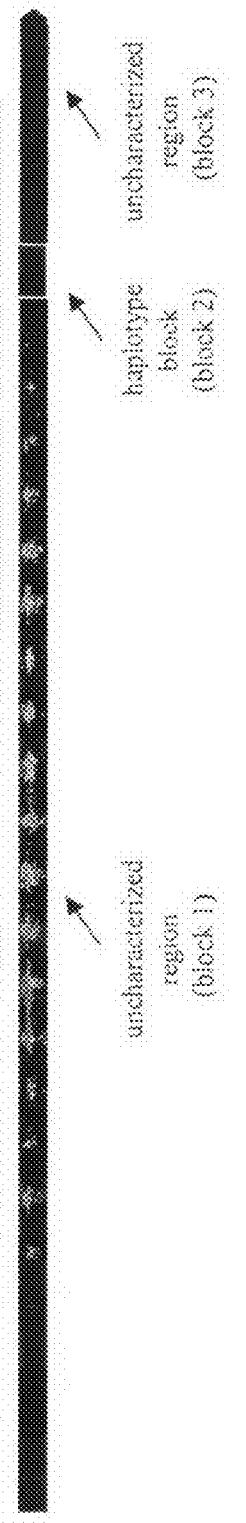
*Figure 1C    Linkage Blocks at IGF2 – Gaunt et al., Human Molec. Genet. 2001, vol. 10, no. 14, 1491-1501*

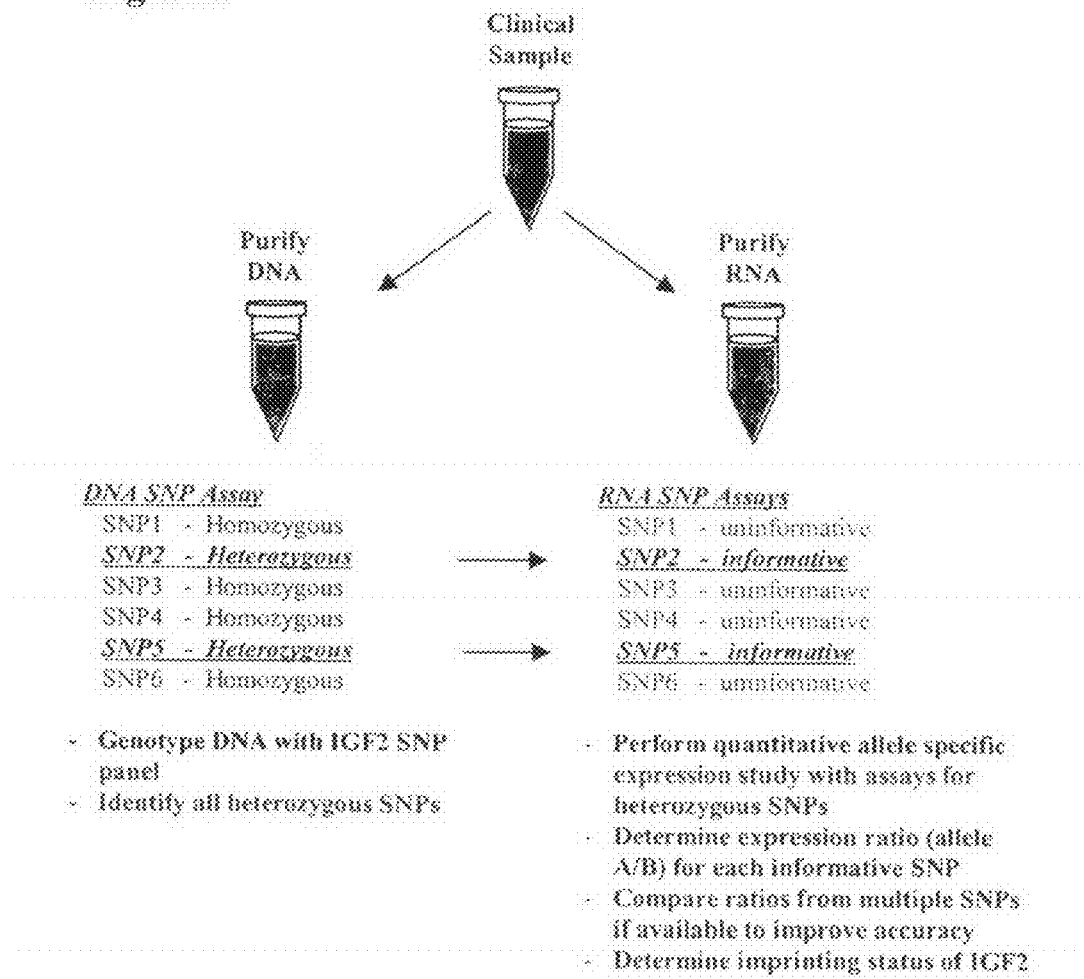

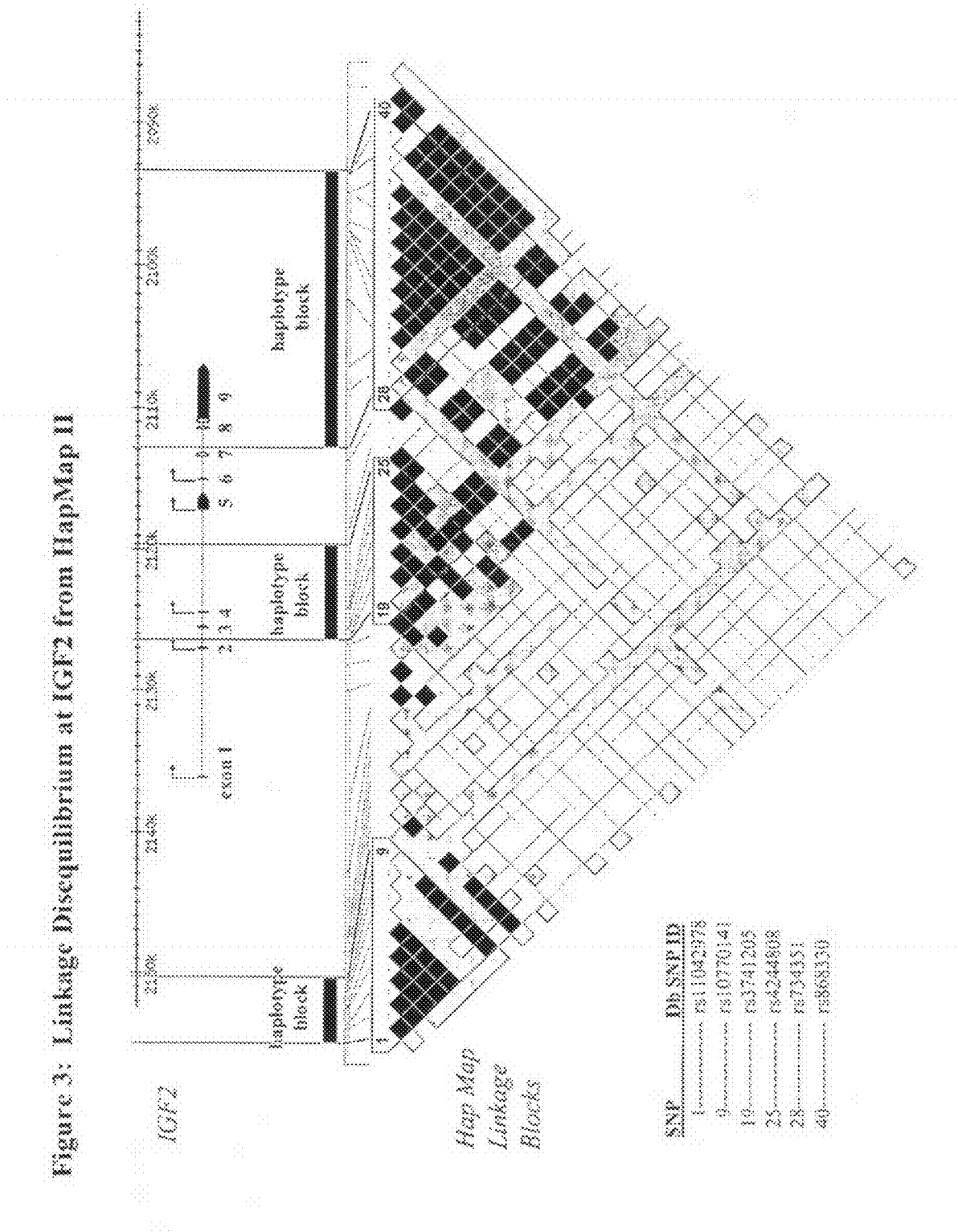

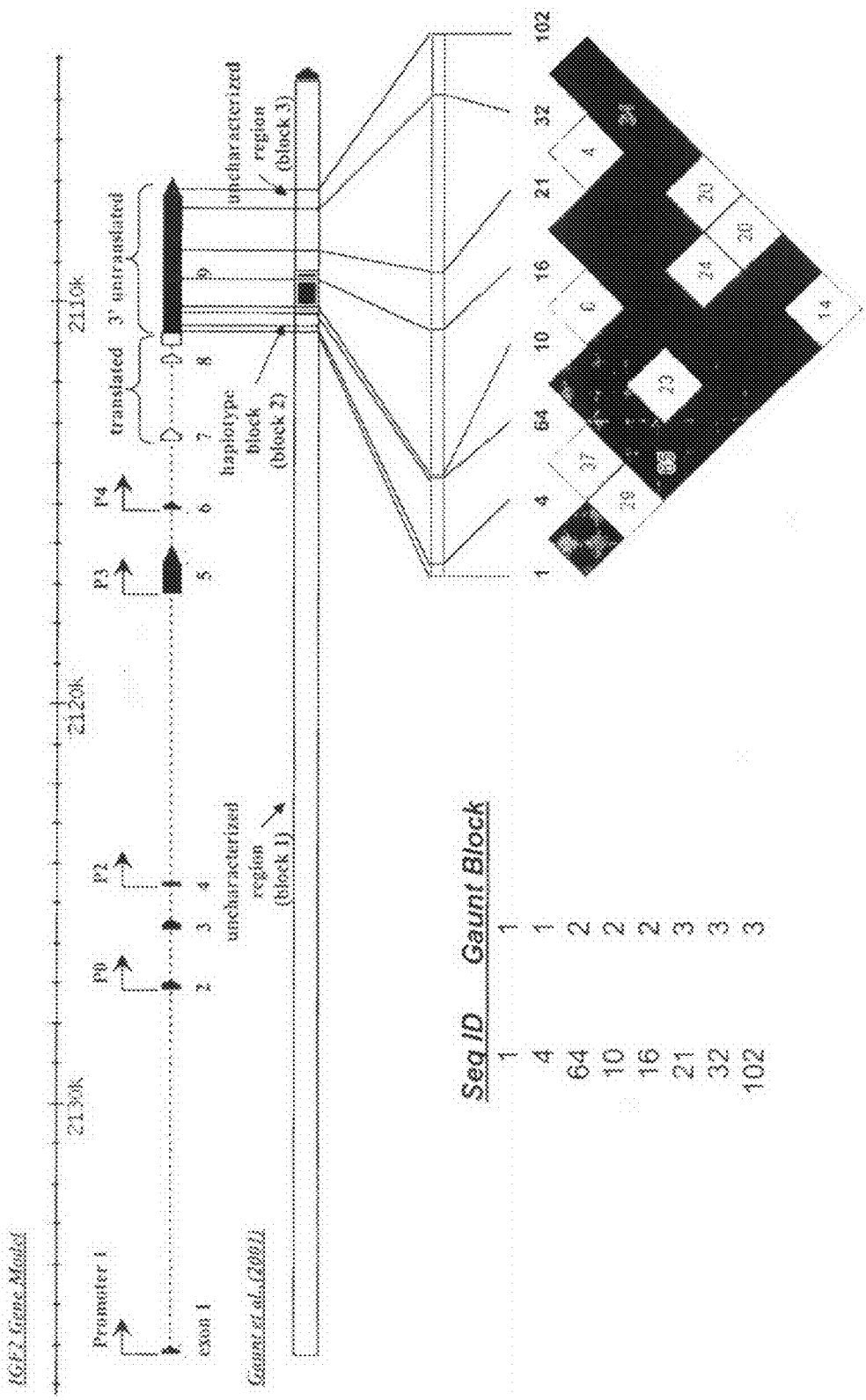

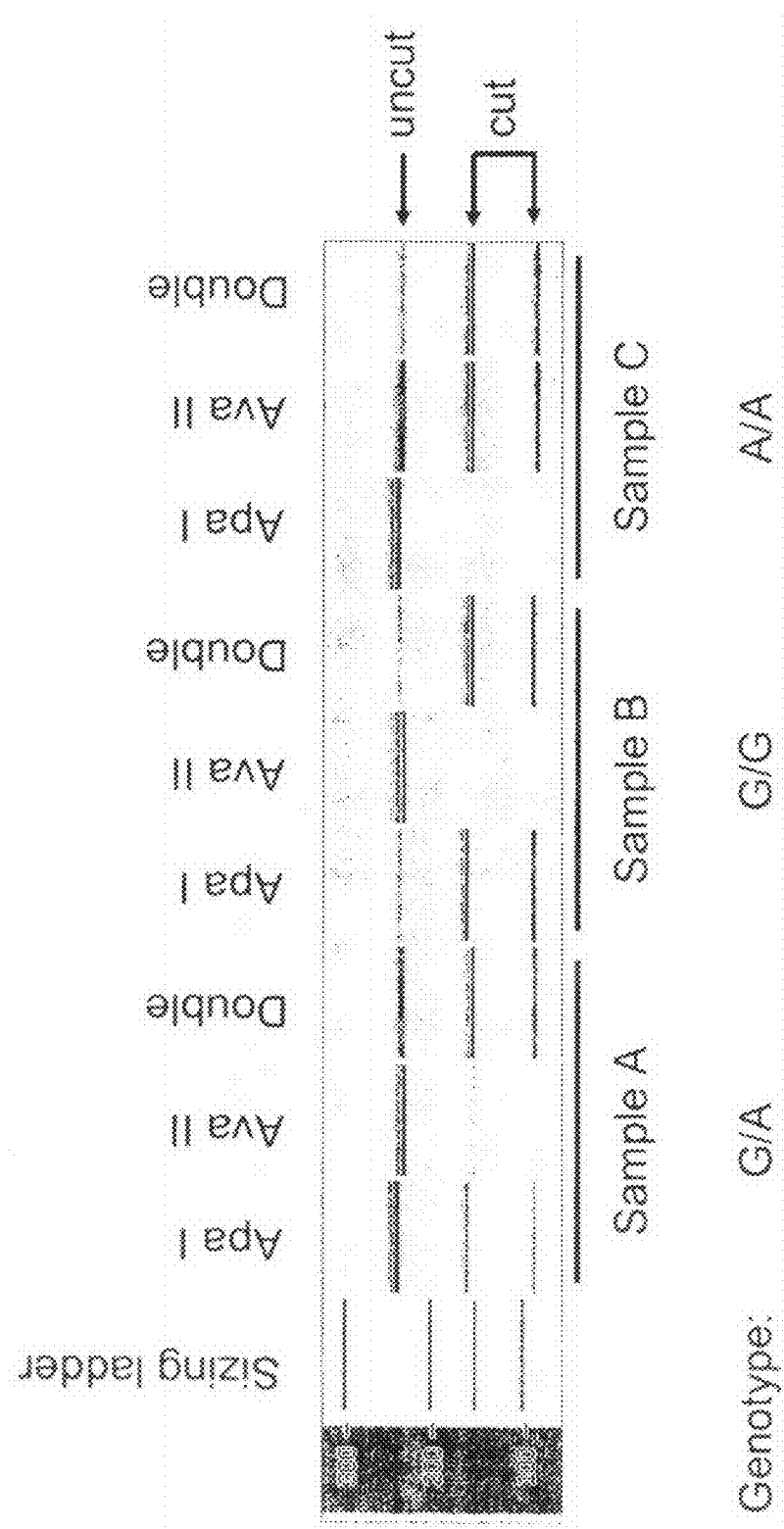
Figure 5. Example of Restriction Enzyme Based Assay for Genotyping SEQ ID 64

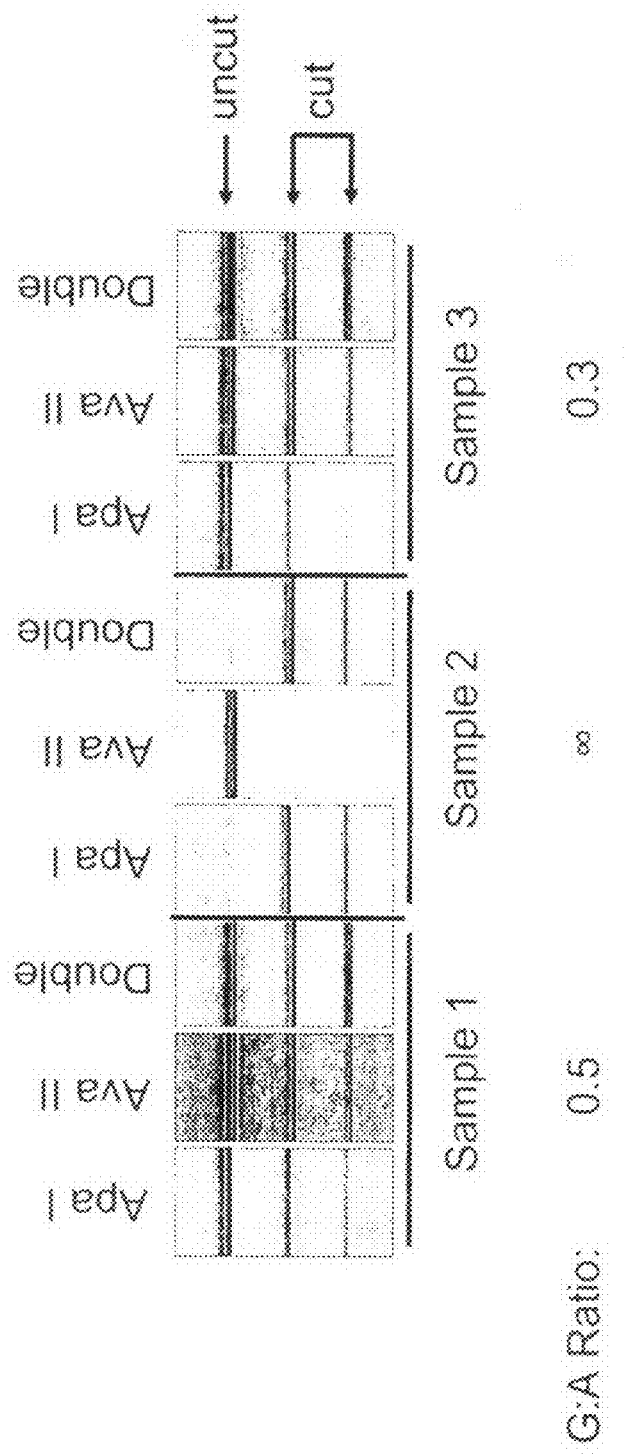
Figure 6. Example of Restriction Enzyme Based Assay for Detecting LOI of IGF2.

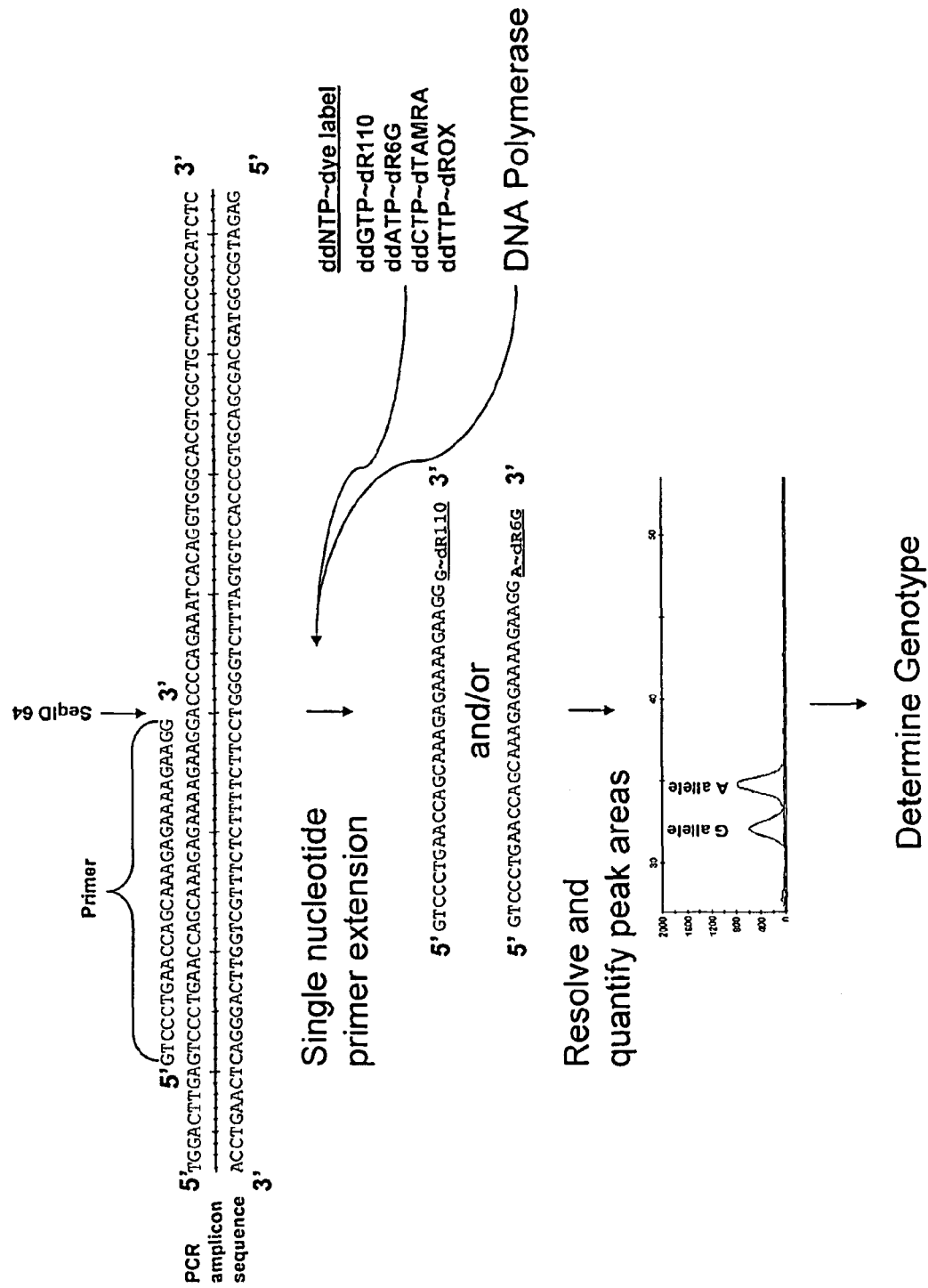
Figure 7. Diagram of Single Nucleotide Primer Extension Assay.

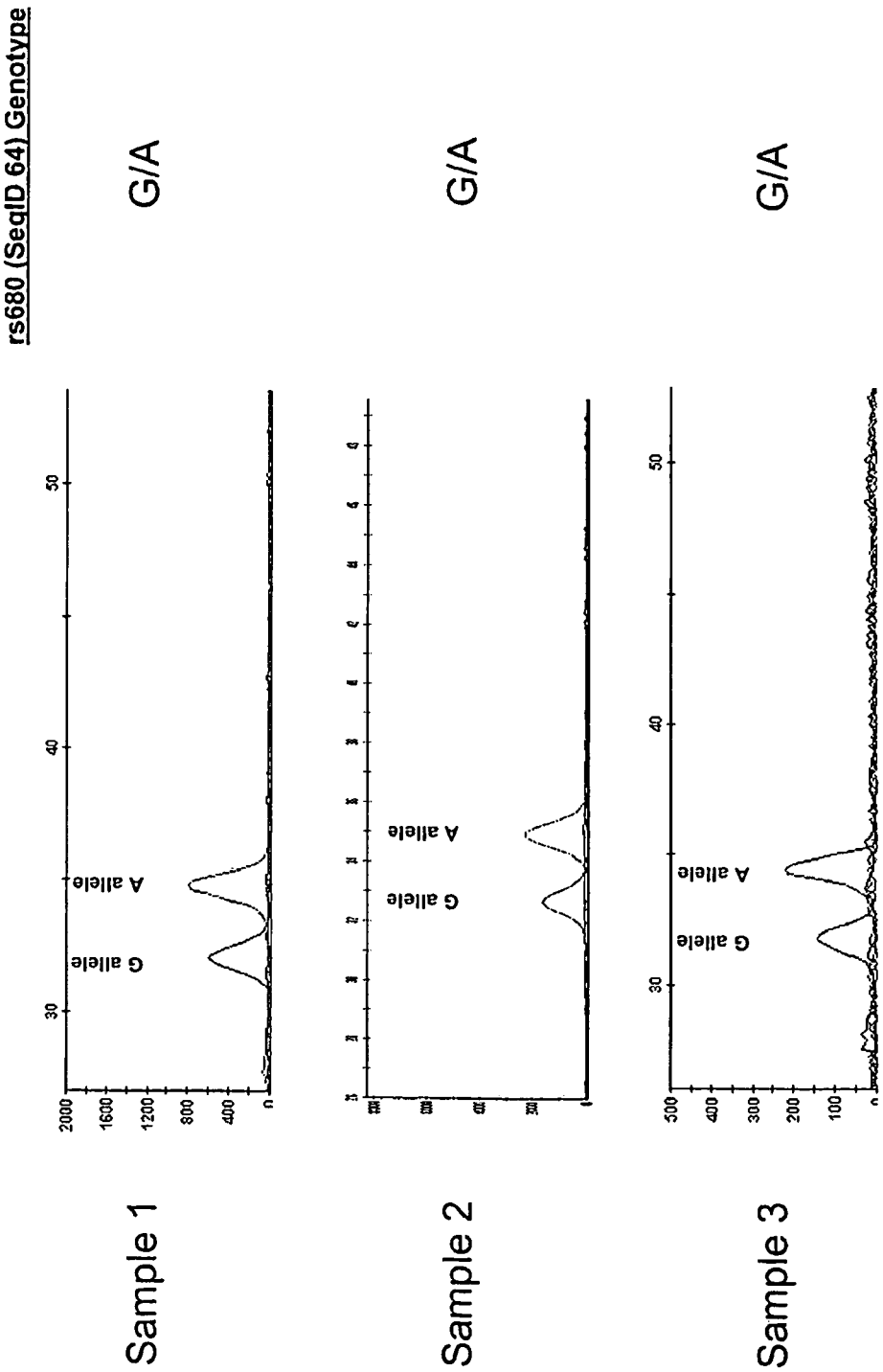
Figure 8. Single Nucleotide Primer Extension Genotyping of SEQ ID 64.

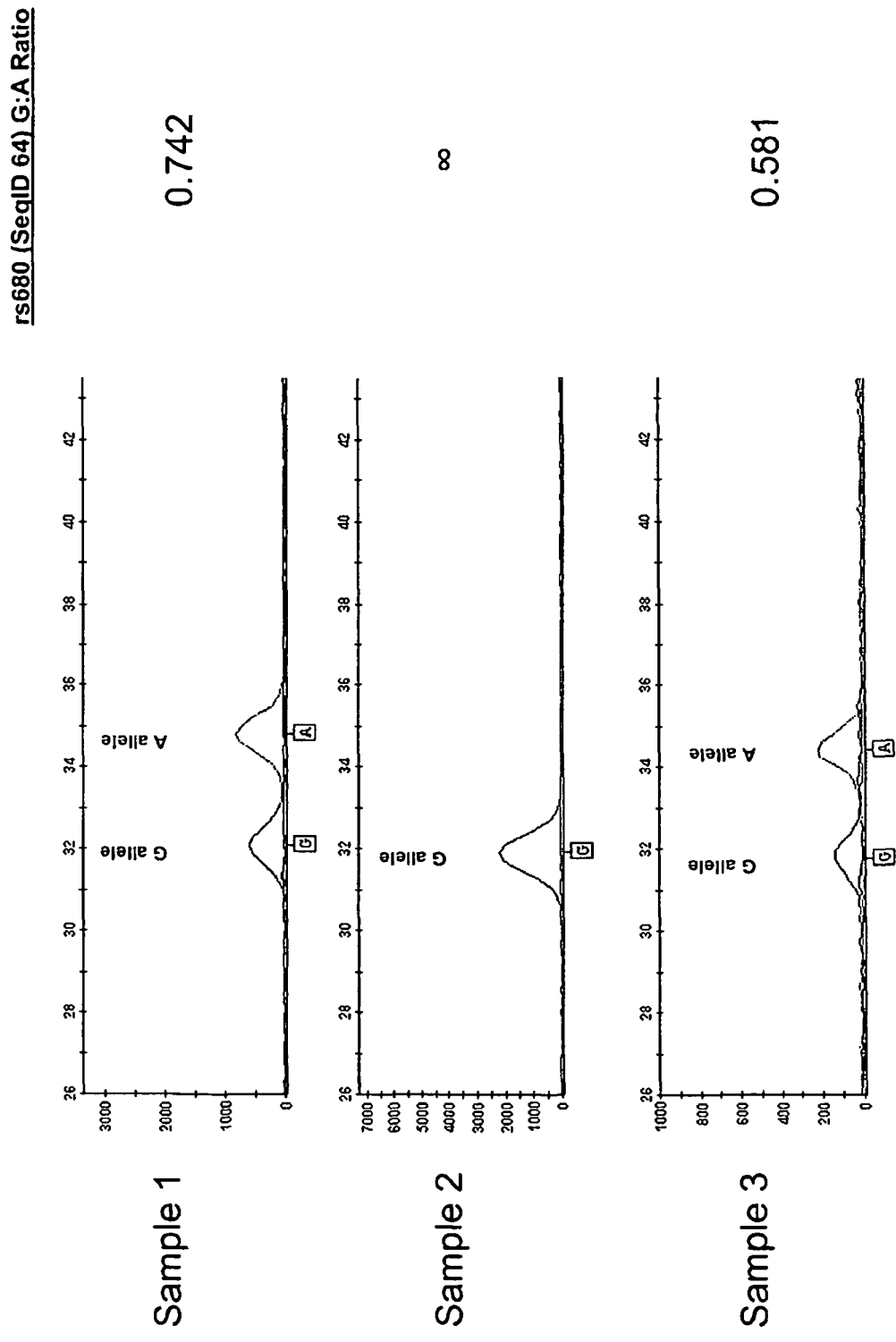
Figure 9. Single Nucleotide Primer Extension Assay Detects LOI of *IGF2*.

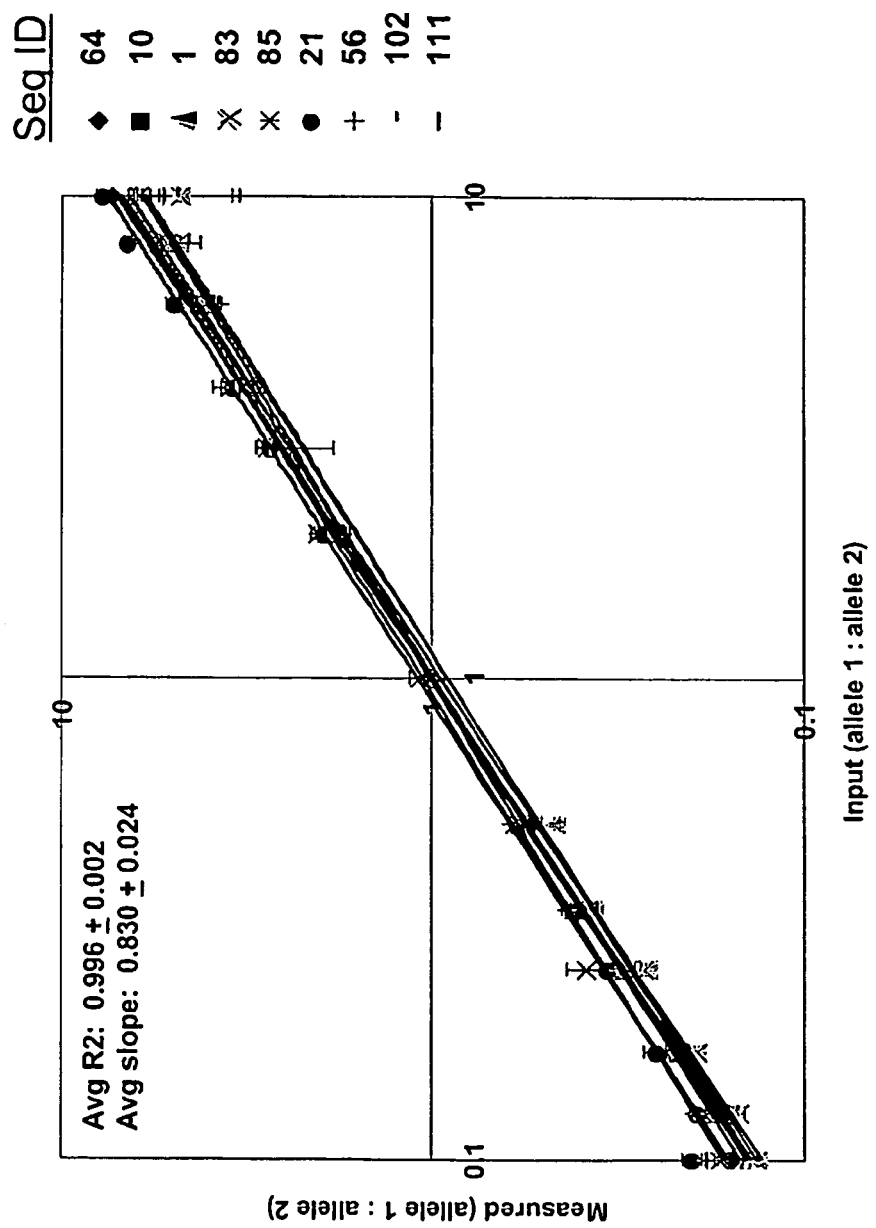
Figure 10. Quantitative Analytical Linearity of Single Nucleotide Primer Extension Assays for Nine Independent SNPs.

US 8,420,315 B2

SINGLE NUCLEOTIDE POLYMORPHISMS AND COMBINATIONS OF NOVEL AND KNOWN POLYMORPHISMS FOR DETERMINING THE ALLELE-SPECIFIC EXPRESSION OF THE IGF2 GENE

CROSS-REFERENCE TO RELATED PATENT APPLICATIONS

The present application is the U.S. National Stage entry of International Application No. PCT/US2008/072356, filed Aug. 6, 2008, which claims benefit of priority to US Provisional Patent Application No. 60/954,290, filed Aug. 6, 2007 and US Provisional Patent Application No. 60/988,715, filed Nov. 16, 2007, each of which are incorporated by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -25-2.TXT, created on Sep. 26, 2012, 36,864 bytes, machine format IBM-PC, MS-Windows operating system, is hereby incorporated by reference in its entirety for all purposes.

BACKGROUND OF THE INVENTION

The gene for insulin-like growth factor 2, or IGF2, is located in a cluster of imprinted genes on human chromosome 11p15.5. Genomic imprinting is an important mechanism of gene regulation where one copy of the gene is normally expressed and the other copy is silenced through an epigenetic mark of parental origin. IGF2 is normally maternally imprinted in human tissues and therefore, expressed only from the paternally inherited copy of the gene (DeChiara T M, et al. *Cell* 64, 849-859 (1991); Rainier S, et al., *Nature* 362, 747-749 (1993); Ogawa, et al, *Nature* 362, 749-751 (1993)). Loss of imprinting of IGF2 (referred to as loss of imprinting, or LOI) has been strongly linked to several cancer types (over 20 tumor types reviewed in Falls, et al. 1999, *AJP* 154, 635-647). Furthermore, mounting evidence indicates that individuals displaying LOI of IGF2 may be at elevated risk for developing colorectal cancer (Kinochi et al., 1996, Cancer Letters 107, 105-108 (1996); Nishihara S. 2000, Int. Jour. Oncol. 17, 317-322; Cui H 1998, Nature Medicine 4-11, 1276-1280; Nakagawa H 2001, PNAS 98-2, 591-596). LOI of IGF2 can be detected in normal tissues of cancer patients including peripheral blood and normal colonic mucosa (Kinochi et al., 1996, Cancer Letters 107, 105-108 (1996); Ogawa, et al, *Nature Genetics* 5, 408-412 (1993); Cui H, *Science* 299, 1753 (2003)) and in the normal tissues of people believed to be cancer free (Cui H, et al. *Nature Medicine* 4-11, 1276-1280 (1998); Cui H, *Science* 299, 1753 (2003); Woodson K et al., JNCI 96, 407-410 (2004); Cruz-Correa M et al., *Gastroenterology* 126, 964-970 (2004)).

Several studies of peripheral blood of general populations report that between 7-10% of people display loss of imprinting of IGF2 in colonic mucosa tissue. Three retrospective studies report that the odds of colorectal cancer patients displaying LOI of IGF2 in either peripheral blood or colonic mucosa are significantly higher (between 2-21 fold) than the odds of an age matched cancer free control group displaying LOI. These studies suggest that LOI of IGF2 may predispose otherwise healthy individuals to colorectal cancer. Therefore, a risk test based on the detection of LOT of IGF2 may have a future clinical benefit, (Cui H, et al. *Nature Medicine* 4-11, 1276-1280 (1998); Cui H, Science 14, 1753-1755 (2003); Woodson K 2004, JNCI 96, 407-410; Cruz-Correa M, Gastroenterology 126, 964-970 (2004)). These studies show that people with LOI of IGF2 (also referred to as the IGF2 biomarker) may be up to 20 times more likely to develop colorectal cancer than individuals without the IGF2 biomarker.

Detection of LOI of IGF2 is based on a quantitative allele specific gene expression assay, where transcripts from both copies of the IGF2 gene are each quantified. The quantities are then compared to one another to determine an allelic gene expression ratio, which is subsequently compared to a threshold value. If the concentration of the lesser abundant allele is "relatively similar" to the concentration of the more abundant allele, then the IGF2 imprint is determined to be lost. If the concentration of the lesser abundant allele is "relatively dissimilar" to the concentration of the more abundant allele, then the IGF2 imprint is determined to be present. One method of measuring the imprinting status of IGF2 in a sample is to first determine the genotype(s) of one or more polymorphic sites in the transcribed region of the IGF2 gene. Heterozygous markers in the transcribed region of the gene provide for convenient molecular handles by which the individual alleles of the IGF2 gene can be distinguished from one another in a sample. RNA transcription from each of the two copies of the IGF2 gene may be independently measured with quantitative allele specific assays. Comparison of the amount of expression of one allele to the amount of expression of the other allele can therefore be made and the imprinting status of the IGF2 gene can be determined (see FIG. 2).

IGF2 has four promoters, each driving expression of alternatively spliced transcripts, in a tissue specific manner (FIG. 1A). Exons 7, 8, and 9 are present in all transcripts, while exons 1-6 have been reported to be expressed in a promoter specific fashion. Exon 9 includes a short stretch of protein-coding sequence followed by a considerably longer 3' UTR. Polymorphic markers in exons 7, 8, and 9 are therefore useful in the determination of IGF2 imprinting status by enabling the detection of allele specific expression of IGF2 transcription driven from any of the four IGF2 promoters.

Four allele-specific expression assays measuring IGF2 imprinting status are known to those skilled in the art. Woodson, et al. measured imprinting status of IGF2 with a combination of two SNP based assays (rs680—analogous to SEQ ID NO: 64 in Table 1A; and rs2230949—analogous to SEQ ID NO: 56 in Table 1A) (Woodson K 2004, JNCI 96, 407-410). Both SNPs are in exon 9 of IGF2 but are reported by Woodson et al. to be in minimal linkage disequilibrium. Therefore attempts to measure LOT of an individual with such a combination of markers increases the probability that the individual will be heterozygous for at least one of the two SNPs, and thereby increase the likelihood that the LOI status of the individual can be determined. The authors demonstrated that the first SNP, the second SNP, or both SNPs were informative (i.e., were heterozygous and, therefore, permitted measurement of LOI of IGF2) in 48 of 106 patients evaluated (or 45%). Cui et al. measured IGF2 imprinting with a combination of two assays, one targeting a SNP (rs680—analogous to SEQ ID NO: 64 in Table 1A) and a second measuring restriction fragment length polymorphisms of a simple sequence repeat within exon 9 of IGF2. The authors demonstrated that the SNP, the repeat, or both markers were informative in 191 of 421 (or 45%) patients evaluated (Cui H, et al. *Nature Medicine* 4-11, 1276-1280 (1998)).

Previous studies have demonstrated that use of these polymorphisms result in a low combined frequency of heterozygosity in patient populations and, therefore, a large number of individuals in these populations were "uninformative" such that their IGF2 imprinting status could not be determined. The present application describes newly discovered SNPs in IGF2 exon 9, and the discovery of useful combinations of SNPs, which enable successful LOT measurements in an increased proportion of the human population. The ability to measure LOI using these polymorphisms in the general population will have a profound medical benefit, serving as the basis for various molecular diagnostic and therapeutic tests.

The informativity of a given SNP for detection of LOT is based on the frequency of heterozygosity of the SNP within a population. Furthermore, the optimal informativity of a combination of different SNPs is dependent upon the linkage among the different markers. For example, if two SNPs fall within a common haplotype block, the combined use of the two SNPs provides a minimal increase in informativity relative to the use of either of the two SNPs alone. However, if two SNPs are not on the same haplotype block (i.e., are in minimal linkage disequilibrium), the combined use of the two SNPs provides an effective increase in informativity relative to the use of either of the two SNPs alone.

The recent release of the HapMap II human genetic variation dataset provides haplotype analysis of genome-wide DNA sequence data. In the HapMap II study, SNPs were identified in 270 people genotyped from four geographically diverse populations, including 30 mother-father-adult child trios from the Yoruba in Ibadan, Nigeria; 30 such trios of northern and western European ancestry living in Utah; unrelated Han Chinese individuals in Beijing and 45 unrelated Japanese individuals in Tokyo. Haplotype analysis of those SNPs within an approximately 70 Kb region including the IGF2 locus provides a view of haplotype blocks predicted by this current and extensive dataset. In FIG. 3, the Haploview visualization of linkage prediction is depicted below a to-scale diagram of the IGF2 locus. Three haplotype blocks are identified (represented as black horizontal bars positioned in scale with the IGF2 locus). The data predict haplotype blocks spanning from approximately 14 to 19 Kb upstream of IGF2 exon 1, from approximately 1 Kb upstream of exon 3 to approximately 5 Kb downstream of exon 4, and from approximately 2 Kb upstream of the start of exon 9 to approximately 14 Kb downstream of the end of exon 9, a haplotype block that encompasses exons 8 and 9. In general, regions between these haplotype blocks display minimal linkage disequilibrium and provide strong evidence for historic recombination (indicated by white diamonds representing multiple pairwise SNP comparisons). These data are summarized in FIG. 1B. Haplotype blocks are represented by black horizontal bars and the region of predicted minimal linkage disequilibrium is represented by a grey horizontal bar.

Gaunt et al. performed an association studying for body mass index (BMI) in a Caucasian cohort of 2,734 European men using 12 SNPs ranging from just upstream of IGF2 exon 1 to approximately 1 Kb prior to the end of the exon 9 3' UTR, (Gaunt et al. Human Mol. Genet. vol. 10, no. 14: 1491-1501). This study included linkage analysis of a single SNP (rs680—analogous to SEQ ID NO: 64 in Table 1A), which had one allele reported to be positively associated with high BMI in the cohort, to each of the other 11 SNPs in a pair wise fashion. The authors report a haplotype block within the 3' UTR of exon 9, containing 3 SNPs from their study (see Example 3 the black horizontal bar in FIG. 1C, and the grey bar in FIG. 4).

BRIEF SUMMARY OF THE INVENTION

The present invention provides methods of determining a SNP genotype in a human individual. In some embodiments, the methods comprise determining, in a sample containing genomic DNA from the individual, the nucleotide or nucleotides at the polymorphic nucleotide of a single nucleotide polymorphism (SNP), wherein the SNP is selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47. In some embodiments, the nucleotide at the polymorphic position of the SNP (and therefore at the corresponding position of the polynucleotide) is an underlined nucleotide as displayed in Table 2A or 2B.

The present invention also provides methods of quantifying allelic-specific expression of RNA in a human individual, wherein the human individual is a heterozygote for a single nucleotide polymorphism (SNP) in the Insulin Growth Factor-2 (IGF2) gene. In some embodiments, the methods comprise quantifying the amount of RNA in a sample from the human individual comprising one or each polymorphic option of the SNP, wherein the SNP is selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47.

In some embodiments, the sample is a blood or tissue sample. In some embodiments, the sample is a stool sample. In some embodiments, the methods further comprise correlating the relative amount of RNA comprising each polymorphic option of the SNP to loss of imprinting of the IGF2 gene. In some embodiments, the correlating step comprises correlating the relative amount of RNA to a prognosis or diagnosis of cancer or a prediction of efficacy of a drug for treating cancer. In some embodiments, the RNA is reverse transcribed into cDNA and the quantity of allele specific cDNA is used to determine the amount of RNA.

In some embodiments, the methods further comprise determining whether the individual is homozygous or heterozygous for one or more SNPs.

The present invention also provides isolated polynucleotides of between 8-100 nucleotides, wherein the polynucleotide distinguishes between one allele of a SNP (or complement thereof) and the other allele of the SNP (or complement thereof) in a hybridization reaction, wherein the SNP is selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47.

In some embodiments, the penultimate or ultimate 3' nucleotide of the polynucleotide hybridizes to the polymorphic nucleotide of the SNP.

The present invention also provides isolated polynucleotides of between 8-100 nucleotides wherein the polynucleotide functions as a primer in Insulin-like Growth Factor 2 (IGF2) cDNA, such that the polynucleotide hybridizes to the cDNA and the 3' nucleotide of the polynucleotide is complementary to the nucleotide immediately upstream of the polymorphic nucleotide of a SNP, wherein the SNP is selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47.

In some embodiments, at least the 10 contiguous 3' nucleotides of the polynucleotide are complementary to the cDNA.

The present invention also provides isolated polynucleotides comprising a SNP sequence, or complement thereof, selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47, wherein the nucleotide at the polymorphic position of the SNP is an underlined nucleotide as displayed in Table 2A or 2B.

The present invention also provides kits comprising an isolated polynucleotide:
of between 8-100 nucleotides wherein the polynucleotide functions as a primer in Insulin-like Growth Factor 2 (IGF2) cDNA, such that the polynucleotide hybridizes to the cDNA and the 3' nucleotide of the polynucleotide is complementary to the nucleotide immediately upstream of the polymorphic nucleotide of a SNP; or
of between 8-100 nucleotides wherein the polynucleotide functions as a primer in Insulin-like Growth Factor 2 (IGF2) cDNA, such that the polynucleotide hybridizes to the cDNA and the 3' nucleotide of the polynucleotide is complementary to the nucleotide immediately upstream of the polymorphic nucleotide of a SNP, wherein the SNP is selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47.

In some embodiments, the kit comprises a first isolated polynucleotide of between 8-100 nucleotides, wherein the polynucleotide distinguishes between a first allele of a SNP and a second allele of the SNP (or complement thereof) in a hybridization reaction.

In some embodiments, the kit further comprises a second isolated polynucleotide of between 8-100 nucleotides, wherein the polynucleotide distinguishes between the first allele of the SNP (or complement thereof) and the second allele of the SNP (or complement thereof), and wherein the first polynucleotide is complementary to the polymorphic nucleotide in the first allele and the second polynucleotide is complementary to the polymorphic nucleotide of the second allele.

In some embodiments, the kit further comprises one or more primer for amplifying a region of the IGF2 locus encompassing the polymorphic site, wherein the one or more primer is different from the isolated polynucleotide.

In some embodiments, the kit further comprises a DNA polymerase. In some embodiments, the polymerase is a thermostable DNA polymerase. In some embodiments, the kit further comprises a reverse transcriptase. In some embodiments, the first and/or second polynucleotide is detectably labeled.

The present invention also provides reaction mixture comprising an isolated polynucleotide: of between 8-100 nucleotides wherein the polynucleotide functions as a primer in Insulin-like Growth Factor 2 (IGF2) cDNA, such that the polynucleotide hybridizes to the cDNA and the 3' terminal nucleotide of the polynucleotide is complementary to the nucleotide immediately upstream of the polymorphic nucleotide of a SNP so that extension of the polynucleotide by a polymerase incorporates a nucleotide complimentary to the polymorphic nucleotide of the SNP; or
of between 8-100 nucleotides wherein the polynucleotide functions as a primer in Insulin-like Growth Factor 2 (IGF2) cDNA, such that the polynucleotide hybridizes to the cDNA and the 3' nucleotide of the polynucleotide is complementary to the nucleotide immediately upstream of the polymorphic nucleotide of a SNP so that extension of the polynucleotide by a polymerase incorporates a nucleotide complimentary to the polymorphic nucleotide of the SNP, wherein the SNP is selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47.

In some embodiments, the reaction mixtures comprise:
a first isolated polynucleotide of between 8-100 nucleotides, wherein the polynucleotide distinguishes between a first allele of a SNP (or a complement thereof) and a second allele of the SNP (or a complement thereof) in a hybridization reaction; a thermostable DNA polymerase; and human genomic DNA or cDNA from reverse-transcription of human RNA.

In some embodiments, the first isolated polynucleotide hybridizes to the DNA. In some embodiments, the polymerase is a thermostable DNA polymerase.

In some embodiments, the reaction mixtures further comprise a second isolated polynucleotide of between 8-100 nucleotides, wherein the polynucleotide distinguishes between the first allele of the SNP (or complement thereof) and the second allele of the SNP (or complement thereof), and wherein the first polynucleotide is complementary to the polymorphic nucleotide in the first allele and the second polynucleotide is complementary to the polymorphic nucleotide of the second allele.

In some embodiments, the reaction mixtures further comprise one or more primer for amplifying a region of the IGF2 locus encompassing the polymorphic site, wherein the one or more primer is different from the isolated polynucleotide.

The present invention provides methods of quantifying allelic-specific expression of RNA in a human individual, wherein the human individual is a heterozygote for at least two single nucleotide polymorphisms (SNPs) in the Insulin Growth Factor-2 (IGF2) gene. In some embodiments, the methods comprise:
quantifying the amount of RNA in a sample from the human individual comprising one or more polymorphic option of each of at least two SNPs, wherein the two SNPs are each selected from "Linkage Block" 1 of Tables 1A, 1B, 1C, 2A or 2B; or
quantifying the amount of RNA in a sample from the human individual comprising one or each polymorphic option of each of at least two SNPs, wherein the at least two SNPs are each selected from "Linkage Block" 2 of Tables 1A, 1B, 1C, 2A or 2B; or
quantifying the amount of RNA in a sample from the human individual comprising one or each polymorphic option of each of at least two SNPs, wherein the at least two SNPs are each selected from "Linkage Block" 3 of Tables 1A, 1B, 1C, 2A or 2B.

In some embodiments, the sample is a blood or tissue sample. In some embodiments, the sample is a stool sample. In some embodiments, the method further comprises correlating the relative amount of RNA comprising each polymorphic option of the SNPs to loss of imprinting of the IGF2 gene and/or predisposition for cancer.

In some embodiments, the RNA is reverse transcribed into cDNA and the quantity of allele-specific cDNA is used to determine the amount of RNA.

Definitions

A "thermostable polymerase" refers to a polymerase useful for PCR applications. A thermostable polymerase can generally be heated to 75° C. repeatedly (e.g., at least 20 times for a minute each time) and retain at least 80% of its original activity. Examples of such polymerases include, but are not limited to, Taq polymerase.

A "single nucleotide polymorphism" or "SNP" refers to a site of one nucleotide that varies between alleles.

An "allele" refers to one member of a pair or set of different forms of a gene. In a diploid organism, an individual has two copies of each autosomal gene. For a single nucleotide polymorphism, an individual has two different alleles of the polymorphic nucleotide if the genotype at the polymorphic nucleotide is different on one copy of the gene than the other copy of the gene (i.e. the individual is heterozygous for the polymorphic nucleotide). If an individual has the same genotype at the polymorphic nucleotide on both copies of the gene (i.e. the individual is homozygous for the polymorphic nucleotide), then the individual has two copies of the same allele of the polymorphic nucleotide. A given individual can be homozygous for one polymorphic nucleotide within a gene (two copies of the same allele of the polymorphic nucleotide) and heterozygous for a different polymorphic nucleotide within the same gene (two different alleles of the polymorphic nucleotide).

"Hybridization" refers to the formation of a duplex structure by two single stranded nucleic acids due to complementary base pairing. Hybridization can occur between exactly complementary nucleic acid strands or between nucleic acid strands that contain minor regions of mismatch.

"Target sequence" or "target region" refers to a region of a nucleic acid that is to be analyzed and comprises the polymorphic site of interest.

As used herein, the terms "nucleic acid," "polynucleotide" and "oligonucleotide" refer to nucleic acid regions, nucleic acid segments, primers, probes, amplicons and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA.

A nucleic acid, polynucleotide or oligonucleotide can comprise, for example, phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. For example, a polynucleotide of the invention can contain one or more modified, non-standard, or derivatized base moieties, including, but not limited to, $N^6$-methyl-adenine, $N^6$-tert-butyl-benzyl-adenine, imidazole, substituted imidazoles, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611; 5,955,589; 5,844,106; 5,789,562; 5,750,343; 5,728,525; and 5,679,785.

Furthermore, a nucleic acid, polynucleotide or oligonucleotide can comprise one or more modified sugar moieties including, but not limited to, arabinose, 2-fluoroarabinose, xylulose, and a hexose.

"Haplotype block" refers to a region of a chromosome that contains one or more polymorphic sites (e.g., 1-10) that tend to be inherited together. In other words, combinations of polymorphic forms at the polymorphic sites within a block cosegregate in a population more frequently than combinations of polymorphic sites that occur in different haplotype blocks. Polymorphic sites within a haplotype block tend to be in linkage disequilibrium with each other. Often, the polymorphic sites that define a haplotype block are common polymorphic sites. Some haplotype blocks contain a polymorphic site that does not cosegregate with adjacent polymorphic sites in a population of individuals.

"Linkage disequilibrium" refers to the preferential segregation of a particular polymorphic form with another polymorphic form at a different chromosomal location more frequently than expected by chance. Linkage disequilibrium can also refer to a situation in which a phenotypic trait displays preferential segregation with a particular polymorphic form or another phenotypic trait more frequently than expected by chance.

BRIEF DESCRIPTION OF THE DRAWINGS

FIG. 1A illustrates the structure of the IGF2 gene. The scale bar above the gene diagram is drawn in 1 Kb increments and depicts the location of IGF2 on chromosome 11 (NCBI build 36). The scale bar is also present in FIG. 4. Arrows in FIG. 1A, represent the four promoters of IGF2. Exons 1 to 9 are indicated below the gene diagram. Black shaded exons 1 to 6 are not protein-coding in most transcripts of IGF2. The white exons 7 and 8 are protein-coding, as is the small white region of exon 9. The black shaded region of exon 9 is the 3' UTR.

FIG. 1B illustrates the regions of IGF2 predicted to fall within haplotype blocks (black horizontal bars) and within regions predicted to be in low linkage disequilibrium (grey horizontal bar) based on haplotype analysis of HapMap II genotyping data, as described in the Background section.

FIG. 1C illustrates the region of IGF2 predicted to fall within a haplotype block (black horizontal bars) and within two uncharacterized regions of IGF2 (grey horizontal bars) based on a previous study (Gaunt et al. *Human Mol Genet.* 10(14):1491-1501 (2001)), as described in the Background section and in Example 3.

FIG. 2 illustrates a basic strategy for determining LOI of IGF2 in a biological sample. Genomic DNA and total or polyadenylated RNA are isolated from a biological sample (for example, peripheral blood, peripheral blood mononuclear cells, stool, ect.) from and individual. The genomic DNA sample is used for genotyping of one or more polymorphic markers (DNA SNP Assay). This step determines whether the individual is heterozygous for a specific SNP or combination of SNPs. Any SNP, or combination of SNPs, determined to be heterozygous may be utilized for analysis of allele-specific expression of the IGF2 gene in the matched RNA sample (RNA SNP assay). In the example shown, an individual was determined by an allele-discriminating DNA genotyping assay to be homozygous for hypothetical SNPs 1, 3, 4 and 6 and heterozygous for hypothetical SNPs 2 and 5. cDNA is amplified from the relevant region of the IGF2 transcript using standard reverse transcriptase and PCR methods such that PCR products including at least SNPs 2 and 5 are amplified. Expression from each of the two copies of the IGF2 gene is independently measured using the generated cDNA with a quantitative allele specific gene expression assay, and that can sufficiently discriminate between the two alleles of the gene. Comparison of the amount of expression of one allele relative to the amount of expression of the other allele thereby determines the imprinting status of the IGF2 gene. Assays that discriminate SNPs 2 and 5 may be performed simultaneously, and allele specific expression ratios obtained for each assay can be compared to improve accuracy.

FIG. 3 illustrates the haplotype analysis of HapMap II SNP genotype data, as described in the Background section. The gene diagram of IGF2 (described in FIG. 1A) is shown, with Haploview-generated linkage data represented below. Vertical lines indicate the positions of predicted haplotype blocks (horizontal black bars) relative to the IGF2 gene diagram. Diamonds are shaded based on the linkage data for the indicated pair-wise comparison of SNPs. Black diamonds represent SNP pairs for which there is strong evidence for linkage disequilibrium (D=1 and LOD score≧2). White diamonds represent SNP pairs for which there is strong evidence for historical recombination, indicating minimal linkage disequilibrium (D'<1 and LOD score<2). Grey diamonds represent SNP pairs which provided uninformative data for determination of linkage disequilibrium. dbSNP identifiers for the SNPs defining the boundaries of the predicted haplotype blocks are indicated at the bottom left of the figure. Analysis of HapMap II data supports a haplotype block encompassing exon 9.

FIG. 4 illustrates the haplotype analysis of SNP genotype data for a combined cohort of Caucasian, African American, Chinese, Japanese and Mexican individuals generated by the study described in the present application. The gene diagram of IGF2 is shown. Vertical lines indicate the relative positions of analyzed SNPs, and extend to the Haploview visualization of linkage analysis below. The horizontal grey bar represents the haplotype block, and the horizontal white bars represent the uncharacterized regions of exon 9 as determined by Gaunt et al. (see Background section and Example 3). Shading of diamonds is as described in FIG. 3. The SEQ ID NO: numbers for analyzed SNPs and the previously reported linkage block (Gaunt Block) to which each belongs are indicated at the bottom left.

FIG. 5 illustrates the use of a restriction enzyme based assay for genotyping the SNP corresponding to SEQ ID NO: 64. The polymorphic nucleotide is located within the recognition sequence of two restriction enzymes. Apa I recognizes and cleaves the sequence when the "G" allele is present, and Ava II recognizes and cleaves the sequence when the "A" allele is present. A PCR amplicon including SEQ ID NO: 64 was amplified from three independent genomic DNA samples derived from three individuals (Samples A, B and C). Amplicons were digested with Apa I or Ava II or a combination of both enzymes (Double). Digestion by Apa I only indicates that the individual is homozygous for the G allele (Sample B), digestion by Ava II only indicates that the individual is homozygous for the A allele (Sample C), and digestion by both enzymes indicates that the individual is heterozygous for the SNP (Sample A).

FIG. 6 illustrates the use of a restriction enzyme based method for detecting LOI of IGF2. Total RNA was extracted from three individuals that are heterozygous for SEQ ID NO:64. The region including SEQ ID NO:64 was RT-PCR amplified from each sample. cDNA amplicons were digested with Apa I or Ava II or a combination of both enzymes, as indicated above each lane. Digested products were resolved on an Agilent Bioanalyzer, and concentrations of cut and uncut fragments were determined. The quantity of fragments cut by Apa I represents the proportion of cDNA including the "G" allele. The quantity of fragments cut by Ava II represents the proportion of cDNA including the "A" allele. Therefore, the ratio of Apa I cut fragments to Ava II cut fragments indicates the relative ratio of expression of the two alleles in the original RNA sample. The calculated G:A ratio is shown below each triplet of lanes representing each sample. Sample 2 expresses exclusively the "A" allele. Samples 1 and 3 express both alleles (i.e. display LOI IGF2), with G:A ratios of 0.5 and 0.3, respectively.

FIG. 7 diagrams a method for allele-specific detection of a SNP using a single nucleotide primer extension strategy. The SNP represented by SEQ ID NO:64 and its surrounding DNA sequence are shown as an example ("PCR amplicon sequence"—SEQ ID NO:114). The nucleotide position of SEQ ID NO:64 is indicated by the arrow labeled "SeqID 64". The sequence of the polynucleotide used for single nucleotide primer extension is indicated by the bracket labeled "Primer" (SEQ ID NO:113). The PCR DNA amplicon (or, alternatively a RT-PCR cDNA amplicon) including the sequence of interest is amplified from the sample to be assayed. A primer is added to the purified PCR (or, alternatively RT-PCR) product that anneals with its 3' terminal nucleotide complimentary to the template nucleotide 1 base to the 3' side of the polymorphic nucleotide to be genotyped. Single nucleotide primer extension is carried out using a thermostable DNA polymerase and differentially fluorescently labeled ddNTPs. In this example, either dR110-labeled ddGTP or dR6G-labeled ddATP is added to the 3' end of the primer (generating SEQ ID NOs: 115 and 116, respectively). These labeled polynucleotides are then resolved and the peak areas representative of each possible incorporated nucleotide are calculated. Peak areas are compared to determine the genotype of the individual at that SNP position (or, alternatively the allele-specific gene expression ratio).

FIG. 8 illustrates the use of the single nucleotide primer extension assay described in FIG. 7 to genotype three individuals for SEQ ID NO:64. The three individuals that were assayed for LOT of IGF2 by the restriction enzyme based assay shown in FIG. 6 were genotyped. The figure shows the resulting chromatograms for each sample following resolution and peak detection using an ABI Genetic Analyzer and Gene Mapper software. As expected, peaks representing both alleles of SEQ ID NO:64 are obtained in relatively equal proportions, confirming that the three individuals are heterozygous for SEQ ID NO:64 and demonstrating the concordance between results obtained by the restriction enzyme based method and the single nucleotide primer extension based method.

FIG. 9 illustrates the application of the single nucleotide primer extension based method for detecting LOI of IGF2. The region including SEQ ID NO:64 was RT-PCR amplified from a total RNA sample derived from each of the three individuals genotyped in FIG. 8. The cDNA products obtained were purified and analyzed as diagrammed in FIG. 7. The figure shows the resulting chromatograms for each sample following resolution and peak detection using an ABI Genetic Analyzer and Gene Mapper software. For each sample, peak areas representing each of the two possible alleles were calculated and compared to each other. The calculated G:A ratios are indicated to the right of each chromatogram. Consistent with the results shown in FIG. 6, Samples 1 and 3 were determined to show LOI of IGF2, and Sample 2 was determined to show normal imprinting of IGF2.

FIG. 10 illustrates the quantitative analytical linearity of single nucleotide primer extension assays developed for nine independent SNPs. The SEQ ID number for each assayed SNP is indicated to the right of the graph. For each assay, PCR products were separately amplified from genomic DNA samples derived from two individuals; one homozygous for one allele of the SNP and the other homozygous for the other allele of the SNP. The PCR products were purified and quantified. For each of the nine SNPs, two PCR products (one amplified from the DNA sample homozygous for one allele and the other amplified from the DNA sample homozygous for the other allele) were combined in the following ratios of allele 1 to allele 2; 1:10, 1:8, 1:6, 1:4, 1:3, 1:2, 1:1, 2:1, 3:1, 4:1, 6:1, 8:1 and 10:1. For each of the nine SNPs, the single nucleotide primer extension assay was performed in triplicate on each dilution point. Peak areas representing each of the two possible alleles were calculated (y-axis) and compared to the known input ratio of each allele pair (x-axis). Values are plotted on a log 10 scale. The average $R^2$ of the assays is 0.996±0.002 and the average slope is 0.830±0.024, demonstrating that each assay is capable of sensitively and accurately measuring relative quantitative ratios of each allele pair represented in a sample.

DETAILED DESCRIPTION

I. Introduction

The present invention provides methods of detecting LOT of IGF2 and includes novel single nucleotide polymorphism (SNPs) in the IGF2 gene. Detection of these SNPs, alone or in combination with each other, or in combination with previously known SNPs, provide a valuable new way to detect, for example, loss of imprinting of IGF2. The new SNPs can, alone or in combination, be used to independently monitor expression of each of a human individual's two copies of the IGF2 gene, and can be used to determine the imprinting status of IGF2 in a biological sample. For example, if an individual is heterozygous for a particular IGF2 SNP, then probes or other reagents can be employed to separately detect and quantify RNA from each IGF2 allele. If one allele is predominantly expressed, then imprinting of IGF2 is likely occurring. However, if both alleles are expressed at similar levels, it is likely that loss of imprinting of IGF2 has occurred.

Further, it is now possible to monitor loss of imprinting in many more human genetic and racial backgrounds. As an example, the present invention provides a number of SNPs that commonly occur in African American, Caucasian, Chinese, Japanese and Mexican populations, thereby allowing for more useful methods for determining cancer risk in those populations than ever before.

In addition to the discovery of novel IGF2 SNPs, the present invention also provides for combinations of IGF2 SNPs that provide a surprising improvement in the ability to detect LOI in individuals compared to what was predicted previously. For example, prior research into genetic recombination frequency at the IGF2 locus described the existence of blocks of low recombination, indicating that there would be no advantage for using two or more SNPs within the same block. See, e.g., HapMap II (NCBI build 36); Gaunt et al., supra. These blocks are depicted in FIGS. 1B and 1C. However, as shown in the data presented herein (see, e.g., FIG. 4), there is in fact substantial recombination within these "blocks" and therefore detection of two or more SNPs within these "blocks" provides a substantial improvement in the ability to detect LOI in individuals than was predicted in the prior art.

Accordingly, the invention provides for the combination of SNPs (either as first described herein or as previously known) that are surprisingly effective in improving the accuracy of LOI determination as well as expanding the possible populations of people for which the assay will be effective (where a person is heterozygous for at least one SNP).

II. IGF2 SNPs

The following sequence identifiers represent SNP sequences within the IGF2 locus selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, and 112.

In one embodiment, the invention provides isolated nucleic acids that comprise at least one SNP having one or the other polymorphic sequence, wherein the SNP sequences are selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47.

The present invention provides polynucleotides that distinguish between two alleles of a SNP, wherein the SNP is selected from the group consisting of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47.

For example, the present invention provides polynucleotides that hybridize to a first allele of a particular SNP, but does not significantly hybridize to the second allele of the SNP. "Does not significantly hybridize" means that in the presence of equal amounts of both alleles in a sample, the polynucleotide is able to detect the presence of the first allele but does not detect the presence of the second allele to such an extent so as to interfere with the interpretation of the assay. In some embodiments, in the presence of equal amounts of both alleles in a sample, the polynucleotide provides a signal for a sample having the first allele that is at least, e.g., about 100; 1,000; 10,000; 100,000 times or more than the signal generated by the polynucleotide for a sample having an equal amount of the second allele. "Signal" refers to any output indicative of hybridization of the polynucleotide to a complementary sequence. In some embodiments, at least 70%, 80%, 90%, 95% of the sequence of the polynucleotide is complementary to a SNP selected from SEQ ID NO:s 1-112, for example, they have at least 8, 10, 15, 20, 30, 40, 50 complementary nucleotides.

Alternatively, the polynucleotides can distinguish between two alleles of a SNP by acting as a primer in a template-specific primer extension reaction. In these embodiments, the polynucleotides do not generally encompass the polymorphic nucleotide but instead hybridize to the genomic DNA such that 3' extension of the polynucleotide occurs at the polymorphic nucleotide. Thus, in some embodiments, the 3' end of the polynucleotide is complementary to a nucleotide within 10, 5, 3, 2, or 1 nucleotide(s) upstream from the polymorphic nucleotide. In some embodiments, the polynucleotides are complementary over at least 70%, 80%, 90%, 95%, 96%, 97%, 98%, 99%, or 100% of the polynucleotides length to an IGF2 cDNA. In some embodiments, the polynucleotide comprises at its 3' end, at least 2, 3, 4, 5, 6, 7, 8, 9, 10, 20, 30, 40, 50, or more contiguous nucleotides that are at least 70%, 80%, 90%, 95%, 96%, 97%, 98%, 99%, or 100% complementary to an IGF2 cDNA. Optionally, the 5' end of the polynucleotide will comprise a sequence tag or other sequence not complementary to an IGF2 cDNA. As is well known in the art, a variety of primer extension methods can be employed to detect SNPs.

In some embodiments, the polynucleotides that distinguish between the two alleles are at least 4, 6, 8, 10, 12, 15, 20, 30, 50, or more nucleotides in length. In some embodiments, the polynucleotides are no more than 1000, 500, 200, 100, 80, 50, 40, 30, or 25 nucleotides in length. For example, the polynucleotides can be, e.g., 8-25, 8-30, 8-50, 8-100, 10-25, 10-50, 10-100, nucleotides, etc. The polynucleotides that distinguish between the two alleles will typically include a nucleotide that corresponds (i.e., aligns with) and is complementary to one of the polymorphic nucleotides of the SNP. In some embodiments, the ultimate or penultimate 3' nucleotide of the polynucleotide is complementary to a nucleotide at the polymorphic position of the SNP. Such embodiments can be particularly useful in SNP detection methods employing the polynucleotides as primers or probes, for example in amplification-based assays such as those involving the polymerase chain reaction.

The polynucleotides of the invention can be detectably labeled. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like, see, e.g., Molecular Probes, Eugene, Oreg., USA), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Hybridization reaction conditions can vary depending on the assay that is used to detect the SNPs. Stringent, sequence-specific hybridization conditions, under which an oligonucleotide will hybridize only to the exactly complementary target sequence, are well known in the art. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridizing conditions will allow sequence mismatches to be tolerated; the degree of mismatch tolerated can be controlled by suitable adjustment of the hybridization conditions.

For Southern-type hybridization, exemplary conditions are: 50% formamide, 5×SSC, and 1% SDS, incubating at 42° C., or 5×SSC, 1% SDS, incubating at 65° C., with wash in 0.2×SSC, and 0.1% SDS at 55° C., 60° C., or 65° C. Such washes can be performed for 5, 15, 30, 60, 120, or more minutes. For PCR applications (involving hybridization and/or extension of primers and/or probes), hybridization conditions comprising annealing and extension condition are well known, e.g., as described in *PCR Protocols: A Guide to Methods and Applications* (Innis et al., eds., 1990).

The present invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

III. Methods for Measuring Loss of Imprinting and Cancer Predisposition

Detection of LOI is based on a comparison of the amount of expression derived from each of the two copies of the IGF2 gene within a biological sample from an individual. Thus, if an individual has two different alleles of the IGF2 gene, then allele-specific detection can be used to quantify expression of each copy of the gene. If imprinting is functioning, then one copy of the gene (typically the maternal copy) will not be expressed in spite of the presence of a genomic copy of the gene. However, if LOI has occurred, then expression will occur from both the maternal and paternal copies of the IGF2 gene. Because expression levels are not always exactly equal when LOI has occurred, in some embodiments, a sample is determined to display LOI of IGF2 if the quantified proportion of the lesser abundant allele is greater than or equal to 33.3% the quantified proportion of the more abundant allele.

It is generally desirable to know whether an individual is heterozygous for a particular SNP. Thus in some embodiments, both DNA (i.e., genomic DNA) and RNA from a sample are obtained. The genomic DNA is assayed to determine whether the individual is heterozygous for a particular SNP. If the individual is heterozygous, then it is possible to measure loss of imprinting by detecting RNA having either of the two SNP alleles and then comparing their expression. This is illustrated in FIG. 2. In some circumstances, however, it may be beneficial to detect only RNA without knowing whether the individual is a heterozygote for a particular SNP. In this circumstance, observing expression of two alleles indicates LOI, while detecting expression of one allele is not informative because it will not be known if the negative result is due to imprinting or homozygosity of the particular SNP. However, by increasing the number of different SNPs detected, it is possible to design an assay such that the chance of an individual being homozygous for every SNP would be extremely low.

In some embodiments, more than one SNP is assayed for an individual. "Assayed" or "assayed for" refers to separately quantifying each possible allele of the SNP. Generally, any combination of SNPs can be assayed for in a sample. In some embodiments, 2, 3, 4, 5, 6, 7, 8, 9, 10, 20, 30, 40, 50, 75, 100, or more different SNPs are assayed to determine whether LOI of IGF2 has occurred. Optimally, amplicons are designed that encompass more than one SNP, thereby allowing for efficient detection of multiple SNPs.

As explained in detail in Example 3, one novel feature of the present invention is the detection of two SNPs in general proximity to each other improves both accuracy of the assay as well as the number of possible heterozygous candidates. This latter finding is particularly surprising in view of earlier reports implying that certain genomic regions segregate as linkage blocks. In view of the discoveries described in Example 3, another novel feature of the present invention is the detection of the relative amounts of the polymorphic options of two or more SNPs, wherein each SNP is selected from the same "Block" as listed in Tables 1A, 1B, 1C, 2A and 2B. Thus, for example, two or more SNPs are assayed for in Block 1. Or, two or more SNPs are assayed for in Block 2. Or, two or more SNPs are assayed for in Block 3. These options do not preclude further addition of SNPs from other Blocks. Simply as an example, this means that two SNPs from Block 1 and one SNP from Block 2 could be assayed for.

As shown in Tables 4-8, various racial groups display different occurrence rates of heterozygosity for the SNPs. Thus, in some embodiments, SNPs are selected for use within a particular racial group to allow for improved chance of assaying for SNPs that are heterozygous in a particular racial group. Thus, in some embodiments, one or more SNPs in Table 4 are assayed for in people of Chinese descent, one or more SNPs in Table 5 are assayed for in people of Japanese descent, one or more SNPs in Tables 6 are assayed for in people of African descent, one or more SNPs in Table 7 are assayed for in Caucasian people, and one or more SNPs in Table 8 are assayed for in people of Mexican descent.

Alternatively, one set of SNPs can be selected to allow for the greatest chance of assaying for a heterozygous SNP regardless of race. Thus, in some embodiments, a panel of SNPs selected from Tables 4-8 are used.

In further embodiments, a person of a certain racial group as listed in Tables 4-8 is tested with one or more SNPs having the same Linkage Block as listed in Tables 1A-C and 2A-B for that same racial group.

IV. Methods of SNP Detection

Detection techniques for evaluating nucleic acids for the presence of a SNP involve procedures well known in the field of molecular genetics. Further, many of the methods involve amplification of nucleic acids. Ample guidance for performing is provided in the art. Exemplary references include manuals such as PCR Technology: *Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Current Protocols in Molecular Biology, Ausubel, 1994-1999, including supplemental updates through April 2004; Sambrook & Russell, *Molecular Cloning, A Laboratory Manual* (3rd Ed, 2001).

Although the methods typically employ PCR steps, other amplification or non-amplification-based protocols may also be used. Suitable amplification methods include ligase chain reaction (see, e.g., Wu & Wallace, *Genomics* 4:560-569, 1988); strand displacement assay (see, e.g., Walker et al., *Proc. Natl. Acad. Sci. USA* 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173-1177, 1989); and self-sustained sequence replication (3SR) (Guatelli et al., *Proc. Natl. Acad. Sci. USA* 87:1874-1878, 1990; WO 92/08800). Alternatively, methods that amplify the probe to detectable levels can be used, such as Qβ-replicase amplification (Kramer & Lizardi, *Nature* 339:401-402, 1989; Lomeli et al., *Clin. Chem.* 35:1826-1831, 1989). A review of known amplification methods is provided, for example, by Abramson and Myers in *Current Opinion in Biotechnology* 4:41-47, 1993.

Typically, detecting SNPs in an individual is performed using oligonucleotide primers and/or probes. Oligonucleotides can be prepared by any suitable method, usually chemical synthesis. Oligonucleotides can be synthesized using commercially available reagents and instruments. Alternatively, they can be purchased through commercial sources. Methods of synthesizing oligonucleotides are well known in the art (see, e.g., Narang et al., *Meth. Enzymol.* 68:90-99, 1979; Brown et al., *Meth. Enzymol.* 68:109-151, 1979; Beaucage et al., *Tetrahedron Lett.* 22:1859-1862, 1981; and the solid support method of U.S. Pat. No. 4,458,066). In addition, modifications to the above-described methods of synthesis may be used to desirably impact enzyme behavior with respect to the synthesized oligonucleotides. For example, incorporation of modified phosphodiester linkages (e.g., phosphorothioate, methylphosphonates, phosphoami- date, or boranophosphate) or linkages other than a phosphorous acid derivative into an oligonucleotide may be used to prevent cleavage at a selected site. In addition, the use of 2'-amino modified sugars tends to favor displacement over digestion of the oligonucleotide when hybridized to a nucleic acid that is also the template for synthesis of a new nucleic acid strand.

The amount and/or presence of an allele of a SNP of the invention in a sample from an individual can be determined using many detection methods that are well known in the art. A number of SNP assay formats entail one of several general protocols: hybridization using allele-specific oligonucleotides, primer extension, allele-specific ligation, sequencing, or electrophoretic separation techniques, e.g., singled-stranded conformational polymorphism (SSCP) and heteroduplex analysis. Exemplary assays include 5' nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. Two methods that can also be used are assays based on invasive cleavage with Flap nucleases and methodologies employing padlock probes.

Determining the presence or absence of a particular SNP allele is generally performed by analyzing a nucleic acid sample that is obtained from a biological sample from the individual to be analyzed. While the amount and/or presence of a SNP allele can be directly measured using RNA from the sample, often times the RNA in a sample will be reverse transcribed, optionally amplified, and then the SNP allele will be detected in the resulting cDNA.

Frequently used methodologies for analysis of nucleic acid samples to measure the amount and/or presence of an allele of a SNP are briefly described. However, any method known in the art can be used in the invention to measure the amount and/or presence of single nucleotide polymorphisms.

Allele Specific Hybridization

This technique, also commonly referred to as allele specific oligonucleotide hybridization (ASO) (e.g., Stoneking et al., *Am. J. Hum. Genet.* 48:70-382, 1991; Saiki et al., *Nature* 324, 163-166, 1986; EP 235,726; and WO 89/11548), relies on distinguishing between two DNA molecules differing by one base by hybridizing an oligonucleotide probe that is specific for one of the variants to an amplified product obtained from amplifying the nucleic acid sample. In some embodiments, this method employs short oligonucleotides, e.g., 15-20 bases in length. The probes are designed to differentially hybridize to one variant versus another. Principles and guidance for designing such probe is available in the art, e.g., in the references cited herein. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA or cDNA such that the polymorphic site aligns with a central position (e.g., within 4 bases of the center of the oligonucleotide, for example, in a 15-base oligonucleotide at the 7 position; in a 16-based oligonucleotide at either the 8 or 9 position) of the probe (e.g., a polynucleotide of the invention distinguishes between two SNP alleles as set forth herein), but this design is not required.

The amount and/or presence of an allele is determined by measuring the amount of allele-specific oligonucleotide that is hybridized to the sample. Typically, the oligonucleotide is labeled with a label such as a fluorescent label. For example, an allele-specific oligonucleotide is applied to immobilized oligonucleotides representing potential SNP sequences. After stringent hybridization and washing conditions, fluorescence intensity is measured for each SNP oligonucleotide.

In one embodiment, the nucleotide present at the polymorphic site is identified by hybridization under sequence-specific hybridization conditions with an oligonucleotide probe exactly complementary to one of the polymorphic alleles in a region encompassing the polymorphic site. The probe hybridizing sequence and sequence-specific hybridization conditions are selected such that a single mismatch at the polymorphic site destabilizes the hybridization duplex sufficiently so that it is effectively not formed. Thus, under sequence-specific hybridization conditions, stable duplexes will form only between the probe and the exactly complementary allelic sequence. Thus, oligonucleotides from about 10 to about 35 nucleotides in length, e.g., from about 15 to about 35 nucleotides in length, which are exactly complementary to an allele sequence in a region which encompasses the polymorphic site are within the scope of the invention (e.g., one of SEQ ID NOs: 1-112).

In an alternative embodiment, the amount and/or presence of the nucleotide at the polymorphic site is identified by hybridization under sufficiently stringent hybridization conditions with an oligonucleotide substantially complementary to one of the SNP alleles in a region encompassing the polymorphic site, and exactly complementary to the allele at the polymorphic site. Because mismatches that occur at non-polymorphic sites are mismatches with both allele sequences, the difference in the number of mismatches in a duplex formed with the target allele sequence and in a duplex formed with the corresponding non-target allele sequence is the same as when an oligonucleotide exactly complementary to the target allele sequence is used. In this embodiment, the hybridization conditions are relaxed sufficiently to allow the formation of stable duplexes with the target sequence, while maintaining sufficient stringency to preclude the formation of stable duplexes with non-target sequences. Under such sufficiently stringent hybridization conditions, stable duplexes will form only between the probe and the target allele. Thus, oligonucleotides from about 10 to about 35 nucleotides in length, preferably from about 15 to about 35 nucleotides in length, which are substantially complementary to an allele sequence in a region which encompasses the polymorphic site, and are exactly complementary to the allele sequence at the polymorphic site, are within the scope of the invention.

The use of substantially, rather than exactly, complementary oligonucleotides may be desirable in assay formats in which optimization of hybridization conditions is limited. For example, in a typical multi-target immobilized-probe assay format, probes for each target are immobilized on a single solid support. Hybridizations are carried out simultaneously by contacting the solid support with a solution containing target DNA or cDNA. As all hybridizations are carried out under identical conditions, the hybridization conditions cannot be separately optimized for each probe. The incorporation of mismatches into a probe can be used to adjust duplex stability when the assay format precludes adjusting the hybridization conditions. The effect of a particular introduced mismatch on duplex stability is well known, and the duplex stability can be routinely both estimated and empirically determined, as described above. Suitable hybridization conditions, which depend on the exact size and sequence of the probe, can be selected empirically using the guidance provided herein and well known in the art. The use of oligonucleotide probes to detect single base pair differences in sequence is described in, for example, Conner et al., 1983, Proc. Natl. Acad. Sci. USA 80:278-282, and U.S. Pat. Nos. 5,468,613 and 5,604,099, each incorporated herein by reference.

The proportional change in stability between a perfectly matched and a single-base mismatched hybridization duplex depends on the length of the hybridized oligonucleotides. Duplexes formed with shorter probe sequences are destabilized proportionally more by the presence of a mismatch. In practice, oligonucleotides between about 15 and about 35 nucleotides in length are preferred for sequence-specific detection. Furthermore, because the ends of a hybridized oligonucleotide undergo continuous random dissociation and re-annealing due to thermal energy, a mismatch at either end destabilizes the hybridization duplex less than a mismatch occurring internally. Preferably, for discrimination of a single base pair change in target sequence, the probe sequence is selected which hybridizes to the target sequence such that the polymorphic site occurs in the interior region of the probe.

The above criteria for selecting a probe sequence that hybridizes to a particular SNP apply to the hybridizing region of the probe, i.e., that part of the probe which is involved in hybridization with the target sequence. A probe may be bound to an additional nucleic acid sequence, such as a poly-T tail used to immobilize the probe, without significantly altering the hybridization characteristics of the probe. One of skill in the art will recognize that for use in the present methods, a probe bound to an additional nucleic acid sequence which is not complementary to the target sequence and, thus, is not involved in the hybridization, is essentially equivalent to the unbound probe.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA or cDNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

In the reverse dot-blot (or line-blot) format, the probes are immobilized on a solid support, such as a nylon membrane or a microtiter plate. The target DNA or cDNA is labeled, typically during amplification by the incorporation of labeled primers. One or both of the primers can be labeled. The membrane-probe complex is incubated with the labeled amplified target DNA or cDNA under suitable hybridization conditions, unhybridized target DNA or cDNA is removed by washing under suitably stringent conditions, and the membrane is monitored for the presence of bound target DNA or cDNA.

An allele-specific probe that is specific for one of the polymorphism variants is often used in conjunction with the allele-specific probe for the other polymorphism variant. In some embodiments, the probes are immobilized on a solid support and the target sequence in an individual is analyzed using both probes simultaneously. Examples of nucleic acid arrays are described by WO 95/11995. The same array or a different array can be used for analysis of characterized polymorphisms. WO 95/11995 also describes subarrays that are optimized for detection of variant forms of a pre-characterized polymorphism.

Allele-Specific Primers

The amount and/or presence of an allele is also commonly detected using allele-specific amplification or primer extension methods. These reactions typically involve use of primers that are designed to specifically target a polymorphism via a mismatch at the 3' end of a primer. The presence of a mismatch affects the ability of a polymerase to extend a primer when the polymerase lacks error-correcting activity. For example, to detect an allele sequence using an allele-specific amplification- or extension-based method, a primer complementary to the polymorphic nucleotide of a SNP is designed such that the 3' terminal nucleotide hybridizes at the polymorphic position. The presence of the particular allele can be determined by the ability of the primer to initiate extension. If the 3' terminus is mismatched, the extension is impeded. If a primer matches the polymorphic nucleotide at the 3' end, the primer will be efficiently extended.

Typically, the primer is used in conjunction with a second primer in an amplification reaction. The second primer hybridizes at a site unrelated to the polymorphic position. Amplification proceeds from the two primers leading to a detectable product signifying the particular allelic form is present. Allele-specific amplification- or extension-based methods are described in, for example, WO 93/22456; U.S. Pat. Nos. 5,137,806; 5,595,890; 5,639,611; and 4,851,331.

Using allele-specific amplification-based methods, identification and/or quantification of the alleles require detection of the presence or absence of amplified target sequences. Methods for the detection of amplified target sequences are well known in the art. For example, gel electrophoresis and probe hybridization assays described are often used to detect the presence of nucleic acids.

In an alternative probe-less method, the amplified nucleic acid is detected by monitoring the increase in the total amount of double-stranded DNA in the reaction mixture, is described, e.g., in U.S. Pat. No. 5,994,056; and European Patent Publication Nos. 487,218 and 512,334. The detection of double-stranded target DNA or cDNA relies on the increased fluorescence various DNA-binding dyes, e.g., SYBR Green, exhibit when bound to double-stranded DNA.

As appreciated by one in the art, allele-specific amplification methods can be performed in reactions that employ multiple allele-specific primers to target particular alleles. Primers for such multiplex applications are generally labeled with distinguishable labels or are selected such that the amplification products produced from the alleles are distinguishable by size. Thus, for example, both alleles in a single sample can be identified and/or quantified using a single amplification by various methods.

As in the case of allele-specific probes, an allele-specific oligonucleotide primer may be exactly complementary to one of the polymorphic alleles in the hybridizing region or may have some mismatches at positions other than the 3' terminus of the oligonucleotide, which mismatches occur at non-polymorphic sites in both allele sequences.

5'-Nuclease Assay

The amount and/or presence of an allele can also be determined using a "TaqMan®" or "5'-nuclease assay", as described in U.S. Pat. Nos. 5,210,015; 5,487,972; and 5,804,375; and Holland et al., 1988, *Proc. Natl. Acad. Sci. USA* 88:7276-7280. In the TaqMan® assay, labeled detection probes that hybridize within the amplified region are added during the amplification reaction. The probes are modified so as to prevent the probes from acting as primers for DNA synthesis. The amplification is performed using a DNA polymerase having 5' to 3' exonuclease activity. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

The hybridization probe can be an allele-specific probe that discriminates between the SNP alleles. Alternatively, the method can be performed using an allele-specific primer and a labeled probe that binds to amplified product.

Any method suitable for detecting degradation product can be used in a 5' nuclease assay. Often, the detection probe is labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification.

DNA Sequencing and Single Base or Other Primer Extensions

The amount and/or presence of an allele can also be determined by direct sequencing. Methods include e.g., dideoxy sequencing-based methods and other methods such as Maxam and Gilbert sequence (see, e.g., Sambrook and Russell, supra).

Other detection methods include Pyrosequencing™ of oligonucleotide-length products. Such methods often employ amplification techniques such as PCR. For example, in pyrosequencing, a sequencing primer is hybridized to a single stranded, PCR-amplified, DNA or cDNA template; and incubated with the enzymes, DNA polymerase, ATP sulfurylase, luciferase and apyrase, and the substrates, adenosine 5' phosphosulfate (APS) and luciferin. The first of four deoxynucleotide triphosphates (dNTP) is added to the reaction. DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a Pyrogram™. Each light signal is proportional to the number of nucleotides incorporated. Apyrase, a nucleotide degrading enzyme, continuously degrades unincorporated dNTPs and excess ATP. When degradation is complete, another dNTP is added.

Another similar method for characterizing SNPs does not require use of a complete PCR, but typically uses only the extension of a primer by a single, detectably (e.g., fluorescently)-labeled dideoxyribonucleic acid molecule (ddNTP) that is complementary to the nucleotide to be investigated. The nucleotide at the polymorphic site can be identified via detection of a primer that has been extended by one base and is fluorescently labeled (e.g., Kobayashi et al, *Mol. Cell. Probes*, 9:175-182, 1995). Of course extension products can also be detected based on other types of labels, or by mass-spectrometry, as desired.

In a similar method, PCR amplified target DNA or RT-PCR amplified target cDNA may be used as template for a single nucleotide primer extension reaction whereby a single fluorescently labeled ddNTP complementary to the polymorphic nucleotide is incorporated on the 3' end of a single primer. Each specific ddNTP can be labeled with a different fluorescent dye (eg. ddATP labeled with dR6G, ddCTP labeled with dTAMRA™, ddGTP labeled with dR110 and ddTTP or ddUTP labeled with dROX™). Therefore, single nucleotide extension of the initially unlabeled primer tags the primer with a specific fluorescent dye that identifies the base that was added to the 3' end of the unlabeled primer. Extended primers can be resolved and analyzed to determine the presence and relative quantity of each specific dye-tagged primer, representing the relative quantities of each allele in the target DNA or target cDNA template.

Restriction Fragment Length Polymorphism Analysis

In other embodiments, the amount and/or presence of an allele of a SNP can be determined by differential digestion of amplified target DNA or cDNA when the polymorphic nucleotide of interest lies within the recognition sequence of a restriction enzyme. In one case, one allele of the SNP (the first allele) maintains the recognition sequence of the restriction enzyme and the other allele (the second allele) does not. In this case, the restriction enzyme will cleave the target DNA or cDNA including the first allele, but not the target DNA or cDNA including the second allele. In another case, one allele (the first allele) of the SNP maintains the recognition sequence of a restriction enzyme (the first restriction enzyme) and the other allele (the second allele) maintains the recognition sequence of a different restriction enzyme (the second restriction enzyme). In this case, the first restriction enzyme will cleave the target DNA or cDNA including the first allele, but not the target DNA or cDNA including the second allele. The second restriction enzyme will cleave the target DNA or cDNA including the second allele, but not the target DNA or cDNA including the first allele. The amount and/or presence of alleles can be determined by various methods including, but not limited to, Southern blot hybridization to immobilized restricted fragments and quantification of band intensities, resolution and visualization of restriction fragments by gel electrophoresis, resolution and quantification of restriction fragments by capillary electrophoresis (such as performed using an Agilent BioAnalyzer), or differential quantitative PCR amplification of cleaved versus uncleaved template DNA or cDNA.

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution (see, e.g., Erlich, ed., *PCR Technology, Principles and Applications for DNA Amplification*, W.H. Freeman and Co, New York, 1992, Chapter 7).

Single-Strand Conformation Polymorphism Analysis

Alleles of target sequences can be differentiated using single-strand conformation polymorphism analysis, which identifies base differences by alteration in electrophoretic migration of single stranded PCR products, as described, e.g, in Orita et al., *Proc. Nat. Acad. Sci.* 86, 2766-2770 (1989). Amplified PCR or RT-PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target SNP detection methods often employ labeled oligonucleotides. Oligonucleotides can be labeled by incorporating a label detectable by spectroscopic, photochemical, biochemical, immunochemical, or chemical means. Useful labels include fluorescent dyes, radioactive labels, e.g., $^{32}P$, electron-dense reagents, enzyme, such as peroxidase or alkaline phosphatase, biotin, or haptens and proteins for which antisera or monoclonal antibodies are available. Labeling techniques are well known in the art (see, e.g., Current Protocols in Molecular Biology, supra; Sambrook & Russell, supra).

V. Methods for Quantifying RNA

The presence and quantity of RNA corresponding to a particular SNP can be readily determined according to any method for quantifying RNA. Various methods involving linkage of RNA to a solid support and probing the RNA (e.g., northern blots, dot blots, etc.) can be used.

In some embodiments, the target RNA is first reverse transcribed (e.g., with reverse transcriptase) and then the resulting cDNA is quantified by any methods known in the art (blot hybridization, RT-PCR, etc.) as a surrogate for RNA quantity. Various methods of reverse transcription are known and described, e.g., in Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)), and can involve reverse transcription using either specific or non-specific primers.

In some embodiments, RT-PCR or other quantitative amplification techniques are used to quantify the target RNA. Amplification of cDNA using reactions is well known (see U.S. Pat. Nos. 4,683,195 and 4,683,202; PCR PROTOCOLS: A GUIDE TO METHODS AND APPLICATIONS (Innis et al., eds, 1990)).

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology* 3:1008-1012 (1985)), allele-specific oligonucleotide (ASO) probe analysis (Conner, et al., *PNAS USA* 80:278 (1983)), oligonucleotide ligation assays (OLAs) (Landegren, et al., *Science* 241:1077, (1988)), and the like. Molecular techniques for DNA analysis have been reviewed (Landegren, et al., *Science* 242:229-237 (1988)).

Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol. Biotechnol.* 20(2):163-79 (2002). Amplifications may be monitored in "real time."

In general, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. *Genome Methods* 6:986-94 (1996) with reference to hydrolysis probes.

One method for detection of amplification products is the 5'-3' exonuclease "hydrolysis" PCR assay (also referred to as the TaqMan™ assay) (U.S. Pat. Nos. 5,210,015 and 5,487, 972; Holland et al., *PNAS USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the "TaqMan™" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of a nucleic acids are also known. For example, some methodologies employ one or more probe oligonucleotides that are structured such that a change in fluorescence is generated when the oligonucleotide(s) is hybridized to a target nucleic acid. For example, one such method involves is a dual fluorophore approach that exploits fluorescence resonance energy transfer (FRET), e.g., LightCycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145), Sunrise™ (or Amplifluor™) probes (e.g., Nazarenko et al., *Nuc. Acids Res.* 25:2516-2521, 1997, and U.S. Pat. No. 6,117,635), and probes that form a secondary structure that results in reduced signal without a quencher and that emits increased signal when hybridized to a target (e.g., Lux Probes™).

In other embodiments, intercalating agents that produce a signal when intercalated in double stranded DNA may be used. Exemplary agents include SYBR GREEN™ and SYBR GOLD™. Since these agents are not template-specific, it is assumed that the signal is generated based on template-specific amplification. This can be confirmed by monitoring signal as a function of temperature because melting point of template sequences will generally be much higher than, for example, primer-dimers, etc.

VI. Kits

The invention also provides kits comprising useful components for practicing the methods. In some embodiments, the kit may comprise one or both allele-specific detection polynucleotides (e.g., primers or probes) for a SNP of the invention, which optionally can be fixed to an appropriate support membrane. In some embodiments, the kits comprise a first isolated polynucleotide of between 8-100 nucleotides, wherein the polynucleotide distinguishes between a first allele of a SNP (or a complement thereof) and a second allele of the SNP (or a complement thereof) in a hybridization reaction, and optionally a second isolated polynucleotide of between 8-100 nucleotides, wherein the polynucleotide distinguishes between the first allele of the SNP (or a complement thereof) and the second allele of the SNP (or a complement thereof), and wherein the first polynucleotide is complementary to the polymorphic nucleotide in the first allele and the second polynucleotide is complementary to the polymorphic nucleotide of the second allele. Optionally, the kits comprise one or both allele specific polynucleotides for 2, 3, 4, 5, 6, 7, 8, 9, 10, 20, 50, 100, or more SNPs selected from SEQ ID NOs: 1-112 Such a kit can also contain amplification primers for amplifying a region of the IGF2 locus encompassing the polymorphic site. Alternatively, useful kits can contain a set of primers comprising an allele-specific primer for the specific amplification of the polymorphic alleles. Such a kit may also comprises probes for the detection of amplification products. Alternatively, useful kits can contain a set of primers complementary to sequences 5' to but not including the SNP positions of interest (or complements thereof) for use in primer extension methods as described above.

Other optional components of the kits include additional reagents used for genotyping patients and/or quantifying the relative amount of specific alleles present. For example, a kit can contain a polymerase, labeled or unlabeled substrate nucleoside triphosphates, means for labeling and/or detecting nucleic acid, appropriate buffers for amplification or hybridization reactions, and instructions for carrying out the present method.

VII. Reaction Mixtures

The invention also provides reaction mixtures comprising components for practicing the methods. In some embodiments, the kit may comprise one or both allele-specific detection polynucleotides (e.g., primers or probes) for a SNP (or a complement thereof) of the invention, which optionally can be fixed to an appropriate support membrane. In some embodiments, the reaction mixtures comprise a first isolated polynucleotide of between 8-100 nucleotides, wherein the polynucleotide distinguishes between a first allele of a SNP (or a complement thereof) and a second allele of the SNP (or a complement thereof) in a hybridization reaction, and optionally a second isolated polynucleotide of between 8-100 nucleotides, wherein the polynucleotide distinguishes between the first allele of the SNP (or a complement thereof) and the second allele of the SNP (or a complement thereof), and wherein the first polynucleotide is complementary to the polymorphic nucleotide in the first allele and the second polynucleotide is complementary to the polymorphic nucleotide of the second allele. Optionally, the reaction mixtures comprise one or both allele specific polynucleotides for 2, 3, 4, 5, 6, 7, 8, 9, 10, 20, 50, 100, or more SNPs selected from SEQ ID NO: 1-112. Such reaction mixtures can also contain amplification primers for amplifying a region of the IGF2 locus encompassing the polymorphic site. Alternatively, reaction mixtures can contain a set of primers comprising an allele-specific primer for the specific amplification of the polymorphic alleles. Such a reaction mixture may also comprise probes for the detection of amplification products. Optionally, reaction mixtures comprise a set of primers complementary to sequences 5' to but not including the SNP positions for 2, 3, 4, 5, 6, 7, 8, 9, 10, 20, 50, 100, or more SNPs selected from SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, and 112.

Other optional components of the reaction mixtures include additional reagents used for genotyping patients and/or quantifying the relative amount of specific alleles present. For example, a reaction mixture can contain a polymerase, labeled or unlabeled substrate nucleoside triphosphates, means for labeling and/or detecting nucleic acid, appropriate buffers for amplification or hybridization reactions.

VIII. Cancer Detection

IGF2 LOI is associated with, for example, a predisposition of cancer as well as predicting the efficacy of treatment of cancer using various drugs. See, e.g., WO2004/003003; Kaneda et al. *Proc. Natl. Acad. Sci. USA* 104(52):20926-20931 (2007). Accordingly, detection of LOI in IGF2 as described herein can be used in the diagnosis, prognosis, classification, prediction of cancer risk, detection of recurrence of cancer, and selection of treatment of a number of types of cancers. A cancer at any stage of progression can be detected, such as primary, metastatic, and recurrent cancers. Information regarding numerous types of cancer can be found, e.g., from the American Cancer Society (available on the worldwide web at cancer.org), or from, e.g., *Harrison's Principles of Internal Medicine*, Kaspar, et al., eds., 16th Edition, 2005, McGraw-Hill, Inc. Exemplary cancers that can be detected include bladder, breast, cervical, choriocarcinoma, colorectal neoplasia (colorectal adenoma or colorectal cancer), esophageal, gastric adenocarcinoma, glioma, hepatocellular, acute myeloid leukemia, chronic myelogenous leukemia, lung, medulloblastoma, prostate, mesothelioma, ovarian, renal cell carcinoma, testicular germ cell, and uterine cancer.

The present invention provides methods for determining whether or not a mammal (e.g., a human) has cancer, whether or not a biological sample taken from a mammal contains cancerous cells, estimating the risk or likelihood of a mammal developing cancer, classifying cancer types and stages, monitoring the efficacy of anti-cancer treatment, or selecting the appropriate anti-cancer treatment in a mammal with cancer.

In some embodiments, the biological sample comprises a tissue sample from a tissue suspected of containing cancerous cells. For example, in an individual suspected of having cancer, breast tissue, lymph tissue, lung tissue, brain tissue, or blood can be evaluated. Alternatively, lung, renal, liver, ovarian, head and neck, thyroid, bladder, cervical, colon, endometrial, esophageal, prostate, or skin tissue can be evaluated. The tissue or cells can be obtained by any method known in the art including, e.g., by surgery, biopsy, phlebotomy, swab, nipple discharge, stool, etc. In other embodiments, a tissue sample known to contain cancerous cells, e.g., from a tumor, will be analyzed for the presence or quantity of methylation at one or more of the diagnostic biomarkers of the invention to determine information about the cancer, e.g., the efficacy of certain treatments, the survival expectancy of the individual, etc. In some embodiments, the methods will be used in conjunction with additional diagnostic methods, e.g., detection of other cancer biomarkers, etc.

The methods of the invention can be used to evaluate individuals known or suspected to have cancer or as a routine clinical test, i.e., in an individual not necessarily suspected to have cancer. Further diagnostic assays can be performed to confirm the status of cancer in the individual.

Further, the present methods may be used to assess the efficacy of a course of treatment. For example, the efficacy of an anti-cancer treatment can be assessed by monitoring LOT over time in a mammal having cancer. For example, a reduction or absence of LOI in IGF2 in a biological sample taken from a mammal following a treatment, compared to a level in a sample taken from the mammal before, or earlier in, the treatment, indicates efficacious treatment. Further, a patient can be screened for LOI of IGF2 prior to selection of an appropriate drug for cancer treatment. For example, once LOI is detected, the patient is likely a good candidate for an IGF1R inhibitor. See, e.g., Kaneda et al., supra.

In some embodiments, the methods comprise recording a diagnosis, prognosis, risk assessment or classification, based on the methylation status determined from an individual. Any type of recordation is contemplated, including electronic recordation, e.g., by a computer.

EXAMPLES

The following examples are offered to illustrate, but not to limit the claimed invention.

Example 1

Discovery of Novel SNPs within Exon 9 of the IGF2 Gene

A collection of SNPs within exon 9 of the IGF2 gene have previously been reported. Tables 1A, 1B and 1C list the genomic coordinates (NCBI build 36), single nucleotide sequence variants, NCBI dbSNP reference identifier and surrounding nucleotide sequences of previously identified SNPs (dbSNP build 129). To identify previously uncharacterized SNPs, we designed 15 PCR amplicons that tile the majority of IGF2 exon 9. Each was used to amplify by PCR the genomic DNA derived from a panel of 589 individuals, including 462 samples that are part of the International HapMap Project collection. The panel included 225 Caucasian individuals (98 from Coriell Human Variation Panel including unrelated healthy Caucasian individuals and 127 individuals from which blood samples were commercially obtained), 96 African American individuals (Coriell Human Variation Panel), 96 individuals of Mexican descent (Coriell Human Variation panel of Mexican-American Community of Los Angeles including unrelated individuals, each having either three or four grandparents born in Mexico), 88 Japanese individuals (International Hapmap Project collection including individuals from Tokyo, Japan), and 84 Chinese individuals (International Hapmap Project collection including Han Chinese individuals from Beijing, China). Multiple direct sequencing attempts were made in both directions for all amplicons. Sequences were assembled and aligned, genotypes were scored, and SNPs were identified for each person in the panel by an automated polyphred and polyscan sequencing analysis pipeline. Genotype designations for high heterozygosity frequency SNPs were manually confirmed by manual inspection of sequence chromatograms within CONSED. As an additional measure of the confidence of genotype designations based on sequencing data, an independent restriction enzyme based genotyping assay was designed for the SNP corresponding to SEQ ID NO: 64 in Table 1A, as described in Example 4. Genotype designations were compared to those based on the sequencing data. Seventy individuals from the Caucasian panel were genotyped by both methods. The concordance between genotype designations based on the two independent methods (sequencing and restriction enzyme digestion based assays) was 100%.

Tables 2A and 2B list the genomic coordinates (NCBI build 36) of single nucleotide sequence variants and surrounding nucleotide sequences of novel SNPs discovered in the study described in the present application. The observed frequencies of heterozygosity for selected SNPs (including both novel and previously identified SNPs) in the sequenced panels of all individuals, as well as in the African American, Caucasian, Chinese, Japanese and Mexican individuals are listed in Table 3. The identification of novel SNPs implies that the novel SNPs described in the present application can be useful for improved detection of LOI of IGF2. For example, the observed heterozygosity frequency of SEQ ID 10 among individuals in the African American panel is 17.33%.

This study demonstrates the differential heterozygosity frequencies of both novel and previously identified SNPs between different racial groups. SNPs that were genotyped as heterozygous in at least 2% of individuals within the Chinese, Japanese, African American, Caucasian, and Mexican cohorts are listed in Tables 4-8, respectively. Therefore, the optimal SNP or combinations of SNPs for monitoring LOI of IGF2 can vary between racial groups.

Example 2

Use of any One of the Novel SNPs for Improved Detection of LOI of the IGF2 Gene

As described above, the detection of LOI of the IGF2 gene is based on the independent comparison of the amount of expression derived from each of the two copies of the IGF2 gene isolated from a biological sample from a given individual. The IGF2 gene is normally maternally imprinted, (i.e. the copy inherited from an individual's mother is normally transcriptionally repressed), while the paternally inherited copy of the gene is normally expressed. LOI occurs when the IGF2 maternal imprint is relaxed, resulting in similar expression levels of both the paternally and maternally inherited copies of the gene. One method of measuring the imprinting status of IGF2 in a sample is to first isolate genomic DNA from a biological sample and then determine the genotype(s) of one or more polymorphic sites in the transcribed region of the IGF2 gene. Second, allele-specific expression of IGF2 is then measured by utilizing one or more heterozygous nucleotides in RNA that is extracted from the same biological sample. Expression from each of the two copies of the IGF2 gene may be independently measured with an assay(s) that is quantitative, and that can sufficiently discriminate between the two alleles of one or more heterozygous SNPs within the sample. Third, a ratio of the amount of expression from one allele to the amount of expression of the other allele is computed and compared to a threshold value, thereby determining the imprinting status of the IGF2 gene in the sample.

As an example of the utility of any one or more of the novel SNPs reported in the present application for monitoring LOI of IGF2, one specific intended approach is described here. It is apparent to those skilled in the art that multiple approaches for detection and quantification of SNPs exist, and any of these may be utilized for both the genotyping of genomic DNA from a biological sample for a particular SNP and the quantification of relative levels of each sequence variant present in expressed mRNA of a biological sample. A basic strategy is outlined in FIG. 2. This involves isolating both genomic DNA and total or polyadenylated RNA from a biological sample (for example, peripheral blood, peripheral blood mononuclear cells, colonic mucosa sample, stool sample, ect.) derived from an individual. The genomic DNA sample is then genotyped with assays detecting the alleles of one or more SNP. This step determines what SNPs, if any, may be utilized for analysis of allele-specific expression of the IGF2 gene in the matched RNA sample. If the individual is homozygous for all SNPs evaluated by an assay, the individual is not informative for those SNPs and can not be measured for LOI of IGF2. If the individual is heterozygous (informative) for one or more SNPs, cDNA is amplified from the relevant region of the IGF2 transcript using standard reverse transcriptase/PCR (RT-PCR) methods. Expression from each of the two copies of the IGF2 gene is independently measured using the generated cDNA with an assay that is quantitative, and that can sufficiently discriminate between the two alleles. Computation of the ratio of the amount of expression of one allele relative to the amount of expression of the other allele, and comparison of this ratio to a threshold value determines the imprinting status of the IGF2 gene. If multiple heterozygous SNPs exist for a given sample, assays that discriminate each of the SNPs may be used simultaneously. This allows redundant measurements of allele-specific expression within a sample, and comparison of these measurements may be used to determine the accuracy of the determination of LOI. While a range of threshold values can be used, typically, a sample is classically determined to display LOI of IGF2 if the quantified proportion of the lesser abundant allele is greater than or equal to 33.3% the quantified proportion of the more abundant allele.

One method for genotyping an individual for a given SNP is accomplished by designing an oligonucleotide primer that is complementary to the sequence of the IGF2 gene and that has a 3' terminal nucleotide that is complementary to the IGF2 template nucleotide one base 3' to the template polymorphic nucleotide (see FIG. 7 for example). Assays may be designed to genotype any one or more of the SNPs listed in Tables 1A, 1B, 1C, 2A and 2B. The oligonucleotide primer is combined with and hybridized to the PCR amplified DNA product from the genomic DNA sample in a mixture including all ddNTPs (ddATP, ddCTP, ddGTP, ddTTP (or ddUTP)), each tagged with a different fluorescent moiety. For example, if a G/A polymorphism is to be genotyped (and the G/A nucleotide is on the template strand of the genomic DNA sample), the oligonucleotide primer is designed to hybridize to the complementary template with its 3' terminal nucleotide hybridized to the complementary template nucleotide one base 3' to the template G/A position. Single nucleotide primer extension is catalyzed by a DNA polymerase in the presence of the differentially fluorescently labeled ddNTPs such that oligonucleotides that extend by incorporation of ddCTP (representing the G allele) or by incorporation of ddTTP (representing the A allele) are differentially fluorescently labeled at their 3' termini. Extended oligonucleotides are then resolved by capillary electrophoresis and analyzed in the presence of a fifth-fluorescent dye-labeled size standard. Peaks representing specific single nucleotide primer extension products are detected and quantified to determine the genotype for the given DNA sample. Multiple SNPs may be genotyped in one reaction by multiplexing with oligonucleotides of different lengths designed to terminate just 3' to different polymorphic sites. Different genotypes are obtained based on i) resolution of different length extended oligonucleotides and ii) the specific fluorescent tagged ddNTP incorporated during single nucleotide extension.

One method for determining the imprinting status of IGF2 involves an analogous single nucleotide primer extension approach that is designed to discriminate different alleles of a particular SNP. Assays may be designed to utilize any one or more of the SNPs listed in Tables 1 and 2. If a given SNP is determined to be heterozygous in a genomic DNA sample, first strand cDNA is amplified from the matched RNA sample by a reverse transcriptase (RT) using random hexamer or decamer primers, oligodT primers complementary to polyA tails of mRNA or a primer complementary to a specific region of the IGF2 transcript. Oligonucleotide primers complementary to sequences flanking the SNP site are subsequently used to PCR amplify a cDNA product including the polymorphic site. Alternatively, nested PCR approaches may be used to generate cDNA products. Alternatively, approaches including generation of aRNA from cDNA by linear in vitro transcription, followed by a second reverse transcription reaction using random hexomer or decamer primers or IGF2 transcript-specific primer and subsequent PCR amplification may be used to generate cDNA products. These RT-PCR products are then assayed for the specific sequence variants of the polymorphic site using the same single nucleotide primer extension assay(s) described above. Peaks representing specific single nucleotide primer extension products are detected and quantified. The ratio of the quantified amount of one allele to the other allele is determined. LOI is detected if the quantified proportion of the PCR product representing the lesser abundant allele is greater than or equal to 33.3% the quantified proportion of the PCR product representing the more abundant allele. As described above, multiple heterozygous SNPs may be used to measure LOI in a common reaction by multiplexing with oligonucleotides of different lengths designed to terminate just 3' to different polymorphic sites or with oligonucleotides that incorporate different labeled ddNTPs into the extended primer.

Example 3

Linkage Analysis Indicates Minimal Linkage Disequilibrium Among Numerous SNPs

The present application describes the discovery of numerous novel SNPs in exon 9 of IGF2. These data allowed high resolution haplotype analyses of 589 individuals (see example 1 for a description of the discovery panel). Genotype data was analyzed by Haploview (Broad Institute of MIT and Harvard University) to determine the presence, or absence, of haplotype blocks across the analyzed regions.

FIG. 4 shows haplotype analyses of SNPs distributed throughout the IGF2 exon 9 region in the entire individual panel. SNPs included in the analysis displayed at least 1% heterozygosity frequency within the genotyped individuals.

Across all individuals (FIG. 4), eight SNPs distributed throughout exon 9 were analyzed (SEQ ID NO: 1, SEQ ID NO: 4, SEQ ID NO: 64, SEQ ID NO: 10, SEQ ID NO: 16, SEQ ID NO: 21, SEQ ID NO: 32, SEQ ID NO: 102). Included in the eight SNP subset is SEQ ID 10, which of all novel SNPs included in this study, had the highest heterozygosity frequency within a given cohort (17.33% heterozygosity frequency in the African American cohort). This study demonstrated minimal linkage disequilibrium between SNPs within the previously reported haplotype block (i.e. within "Gaunt Block 2" as indicated in FIG. 4). For example, strong evidence for historical recombination was detected between the high frequency SNP SEQ ID NO: 10 and SEQ ID NO: 16 (indicated by the white diamond in the Haploview output). Minimal linkage disequilibrium was also observed between SNPs within the previously reported haplotype block and SNPs within the up and downstream regions of exon 9 (uncharacterized regions block 1 and block 3). One example of this is the high frequency SNP in block 2, SEQ ID 10, which reported minimal linkage disequilibrium with SEQ ID 102 in block 3. Additional examples of these SNP pairs include SEQ ID NO: 4 and SEQ ID NO: 64; SEQ ID NO: 4 and SEQ ID NO: 16; SEQ ID NO: 64 and SEQ ID NO: 32; and SEQ ID NO: 10 and SEQ ID NO: 102. Surprisingly, and contrary to the finding of Gaunt and of the HAPMAP linkage analysis of this region, we found no evidence for strong linkage disequilibrium. These findings indicate an unexpected frequency of recombination within this relatively small region of genomic sequence. These findings support the conclusion that for this locus, the use of assays detecting more than one polymorphic marker which are collocated on what were believed to be the same prior art "linkage block" will increase the informativity of a test to determine imprinting status of a sample. Panels of markers to be quantified may be based on combinations of SNPs among the previously described SNPs and the novel SNPs described in this application, and these findings demonstrate, counter to what was known prior to our study, that such combinations of markers can improve the ability to monitor LOI of IGF2 by dramatically increasing the percentage of populations that can be tested.

Example 4

Demonstration of Use of SNPs to Determine LOI Status of IGF2

The SNP corresponding to SEQ ID NO: 64 (rs680) falls within the target recognition sequences of two restriction enzymes, Apa I and Ava II. These two enzymes cleave in an allele-specific manner. Apa I recognizes and cleaves the sequence when the "G" allele is present, and Ava II recognizes and cleaves the sequence when the "A" allele is present. To independently assess genotypes within a selected panel of individuals, a PCR amplicon including the position of SEQ ID NO: 64 was amplified from a genomic DNA sample derived from each individual. Amplicons were digested with Apa I or Ava II or a combination of both enzymes. Digestion by Apa I only indicates that the individual is homozygous for the G allele, digestion by Ava II only indicates that the individual is homozygous for the A allele, and digestion by both enzymes indicates that the individual is heterozygous for the SNP. An example of the data output for each possible genotype of SEQ ID NO: 64 is shown in FIG. 5. As described above, the genotype call determined by the digestion-based assay exactly matched the genotype call based on DNA sequencing in 70 of 70 individuals (100%).

The same basic assay strategy can be utilized to detect LOT of IGF2, provided the individual being tested is heterozygous for SEQ ID NO: 64. An example is shown in FIG. 6. Total RNA was extracted from three individuals heterozygous for SEQ ID NO: 64. Two individuals were previously shown to be LOI for IGF2 and the third was previously shown to display normal imprinting of IGF2. The region including SEQ ID NO: 64 was RT-PCR amplified from each sample. Reactions lacking reverse transcriptase were performed in parallel to confirm that there was no amplification from genomic DNA. RT-PCR amplicons were then digested with Apa I or Ava II or a combination of both enzymes, as described above. Digested products were resolved on an Agilent Bioanalyzer, and concentrations of cut and uncut fragments were determined. The quantity of fragments cut by Apa I represents the proportion of cDNA amplified from the "G" allele. The quantity of fragments cut by Ava II represents the proportion of cDNA amplified from the "A" allele. Therefore, the ratio of Apa I cut fragments to Ava II cut fragments indicates the relative ratio of expression of the two alleles in the original RNA sample. As shown in FIG. 6, Sample 2 expresses exclusively the "A" allele. Samples 1 and 3 express both alleles (i.e. display LOI IGF2), with G:A ratios of 0.5 and 0.3, respectively. As described above, previous studies have used a threshold of 33.3% expression from the lesser abundant allele relative to the more abundant allele as the definition for LOT of IGF2.

Other SNPs that can be useful for detecting LOI of IGF2 do not fall within restriction enzyme recognition sequences. Therefore, the ability to monitor LOI in a given individual is improved by developing allele-specific gene expression assays that do not require restriction enzyme digestion. As a demonstration, we developed a primer extension based assay for SEQ ID NO: 64. FIG. 7 diagrams the use of a primer extension assay for genotyping SEQ ID NO: 64. The region including the SNP of interest is PCR amplified using genomic DNA obtained from the individual to be genotyped. A primer is added to the purified PCR product that anneals with its 3' terminal nucleotide complimentary to the template nucleotide 1 base to the 3' side of the polymorphic nucleotide to be genotyped. Single nucleotide primer extension is carried out using a thermostable DNA polymerase and differentially fluorescently labeled ddNTPs. In the example diagrammed in FIG. 7, either dR110 labeled ddGTP or dR6G labeled ddATP is added to the 3' end of the primer. These labeled polynucleotides are then resolved and the peak areas representative of each possible incorporated nucleotide are calculated (i.e. using an ABI 3730 Gene Analyzer with Gene Mapper software). Peak areas are compared to determine the genotype of the individual at that SNP position.

The three individuals that were assayed for LOI of IGF2 by the restriction enzyme based assay (FIG. 6) were genotyped for SEQ ID NO: 64 using the primer extension assay (FIG. 8). As expected, peaks representing both alleles of the SNP were detected, confirming that the three individuals are heterozygous for SEQ ID NO: 64.

To measure allele-specific expression of IGF2 in the same three individuals, the region including SEQ ID NO: 64 was RT-PCR amplified from a total RNA sample derived from each individual. Reactions lacking reverse transcriptase were performed in parallel to confirm that there was no amplification from genomic DNA. The cDNA products obtained were purified and analyzed as diagrammed in FIG. 7. Peak areas representing each of the two possible alleles were calculated. To correct for differences in dye intensities, these values were normalized based on comparisons of peak areas calculated using predetermined 1:1 ratios of each allele (i.e. 1:1 ratio of DNA amplicons derived from individuals that are homozygous for each of the two alleles). The resulting chromatograms and calculated allele ratios are shown in FIG. 9. In agreement with the results shown in FIG. 6, Samples 1 and 3 were determined to show LOI of IGF2, and Sample 2 was determined to show normal imprinting of IGF2. The same type of single nucleotide primer extension assay that utilizes any SNP within the transcribed region of IGF2 could be used to monitor allele-specific expression of IGF2.

To demonstrate the use of additional SNPs for measuring allele-specific expression of IGF2, single nucleotide primer extension assays were designed based on eight additional SNPs (SEQ ID NO: 1, 10, 21, 56, 83, 85, 102 and 111). The SNPs corresponding to SEQ ID NO: 1, 10 and 21 are novel SNPs. For each of the nine SNPs (including SEQ ID NO: 64), PCR products were separately amplified from genomic DNA samples derived from two individuals; one homozygous for one allele of the SNP and the other homozygous for the other allele of the SNP. The PCR products were purified and quantified. For each of the nine SNPs, two PCR products (one amplified from the DNA sample homozygous for one allele and the other amplified from the DNA sample homozygous for the other allele) were combined in the following ratios of allele 1 to allele 2; 1:10, 1:8, 1:6, 1:4, 1:3, 1:2, 1:1, 2:1, 3:1, 4:1, 6:1, 8:1 and 10:1. For each of the nine SNPs, the single nucleotide primer extension assay was performed in triplicate on each dilution point. Peak areas representing each of the two possible alleles were calculated. To correct for differences in dye intensities, these values were normalized based on comparisons of peak areas calculated using predetermined 1:1 ratios of each allele. The analytical quantitative linearity of each assay is shown in FIG. 10. The average $R^2$ of the assays is 0.996±0.002 and the average slope is 0.830±0.024.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 1A

Known Polymorphisms in IGF2 exons 8 & 9.

| Seq. ID | Genomic Position* | dbSNP | Alleles | Block | Sequence |
|---|---|---|---|---|---|
| 48 | 2111395 | rs1803647 | [C/G] | 1 | TGCTGTTTCCGCAGCTGTGACCTGGC[C/G]CTCCTGGAGACGTACTGTGCTACCC |
| 49 | 2110976 | rs14367 | [G/A] | 1 | AGTTCTTCCAATATGACACCTGGAA[G/A]CAGTCCACCCAGCGCCTGCGCAGGG |
| 50 | 2110955 | rs1065443 | [C/T] | 1 | GGAAGCAGTCCACCCAGCGCCTGCG[C/T]AGGGGCCTGCCTGCCCTCCTGCGTG |
| 51 | 2110819 | rs11545014 | [C/T] | 1 | AAGACCCCGCCCACGGGGGCGCCCCC[C/T]CAGAGATGGCCAGCAATCGGAAGTG |
| 52 | 2110818 | rs1050342 | [A/C] | 1 | AGACCCCGCCCACGGGGGCGCCCCCC[A/C]AGAGATGGCCAGCAATCGGAAGTGA |
| 53 | 2110796 | rs12993 | [G/T] | 1 | CCCCCAGAGATGGCCAGCAATCGGAA[G/T]TGAGCAAAACTGCCGCRAGTCTGCA |

TABLE 1A-continued

Known Polymorphisms in IGF2 exons 8 & 9.

| Seq. ID | Genomic Position* | dbSNP | Alleles | Block | Sequence |
|---|---|---|---|---|---|
| 54 | 2110779 | rs9282726 | [A/G] | 1 | CAATCGGAAKTGAGCAAAACTGCCGC[A/G]AGTCTGCAGCCYGGYGCCACCATCC |
| 55 | 2110767 | rs3741214 | [C/T] | 1 | AGCAAAACTGCCGCAAGTCTGCAGCC[C/T]GGCGCCACCATCCTGCAGCCTCCTC |
| 56 | 2110764 | rs2230949 | [C/T] | 1 | AAACTGCCGCAAGTCTGCAGCCCGG[C/T]GCCACCATCCTGCAGCCTCCTCCTG |
| 57 | 2110733 | rs3213234 | [G/T] | 1 | CATCCTGCAGCCTCCTCCTGACCAC[G/T]GACGTTTCCATCAGGTTCCATCCCG |
| 58 | 2110683 | rs34337549 | [−/G] | 1 | CGGGGACTGGGTCAGGAGAAGCCCCA[−/G]GGGGACGTGGAACCGAGAGATTTTC |
| 59 | 2110613 | rs6223 | [A/C] | 1 | CAGGCTACTCTCCTCGGCCCCCTCC[A/C]TCGGGCTGAGGAAGCACAGCAGCAT |
| 60 | 2110586 | rs11510 | [A/T] | 1 | TCGGGCTGAGGAAGCACAGCAGCATC[A/T]TCAAACATGTACAAAATCGATTGGC |
| 61 | 2110554 | rs1803648 | [A/C] | 1 | ATGTACAAAATCGATTGGCTTTAAA[A/C]ACCCTTCACATACCCTCCCCCCAAA |
| 62 | 2110470 | rs11564731 | [−/AC] | 1 | AAAACATTAAACTAACCCCCTTCCC[−/AC]CCCCCCCACAACAACCCTCTTAAAA |
| 63 | 2110279 | rs15737 | [C/T] | 1 | TGGCACTCCCCACCCCCTCTTTCT[C/T]TTCTCCCTTGGACTTTGAGTCAAAT |
| 64 | 2110210 | rs680 | [G/A/C/T] | 2 | CTGAACCAGCAAAGAGAAAAGAAGG[G/A/C/T]CCCCAGAAATCACAGGTGGGCACGT |
| 65 | 2110180 | rs1065685 | [C/G] | 2 | CAGAAATCACAGGTGGGCACGTCGCT[C/G]CTACCGCCATCTCCCTTCTCACGGG |
| 66 | 2109887 | rs56731553 | [C/T] | 2 | GTGCTCGTGTGTGCTGTGTTCATG[C/T]GTGTGCTGTGTGTTGTGTGTGTGTA |
| 67 | 2109881 | rs56154171 | [C/T] | 2 | TGTGCTGTGCTCGTGTGTGCTGTG[C/T]CATGCGTGTGCTGTGTGTTGTGTGT |
| 68 | 2109862 | rs59198946 | [−/AT] | 2 | GTGCTGTGCGTTTGTGTGTGCTGT[−/AT]GCTCGTGTGTGCTGTGTTCATGC |
| 69 | 2109849 | rs61872709 | [C/T] | 2 | TCTGTGTGCTGTGTGTGCTGTGCGTT[C/T]GTGTGTGTGCTGTGCTCGTGTGTGT |
| 70 | 2109847 | rs61872708 | [C/T] | 2 | CATCGTGTGCTGTGTGTGCTGTGCG[C/T]TTGTGTGTGTGCTGTGCTCGTGTGT |
| 71 | 2109730 | rs61872707 | [A/G] | 2 | TGCGTTTGTGTGTGCTGTGTGTGC[A/G]TGTGTGCGTGTGTGTGCCGTGCG |
| 72 | 2109724 | rs61872706 | [A/G] | 2 | GTGCTGTGCGTTTGTGTGTGCTGT[A/G]TGTGCATGTGTGTGCGTGTGTGTGC |
| 73 | 2109712 | rs11042774 | [C/T] | 2 | gtgcgtttgtgtgtgctgtgcgtttg[C/T]gtgtgtgctgtgtgtgcatgtgtgt |
| 74 | 2109604 | rs59630895 | [−/TGTG] | 2 | TTGTGTGTGTGCTGTGTGCTAGTGTG[−/TGTG]CTGTGTGTGCATGTGTGTGCGTGTG |
| 75 | 2109541 | rs7111331 | [C/T] | 2 | tgctgtgttcgtgtgtgctgtgttcg[C/T]gtgtgtgctgtgtgtgcatgtgt |

*Coordinates relative to NCBI Build 36, Chr: 11

TABLE 1B

Known Polymorphisms in IGF2 exon 9.

| Seq. ID | Genomic Position* | dbSNP | Alleles | Block | Sequence |
|---|---|---|---|---|---|
| 76 | 2108682 | rs11042767 | [C/T] | 3 | ACATTTCTTGGGGGGTCCCCAGGAGA[C/T]GGGCAAAGATGATCCCTAGGTGTGC |
| 77 | 2108628 | rs7129583 | [C/T] | 3 | AGTCCTCGGGGCCGTGCACTGATG[C/T]GGGGAGTGTGGGAAGTCTGGCGGTT |
| 78 | 2108395 | rs28462050 | [T/G] | 3 | GCATTTTTCCTTTTTTTTTTTTTT[T/G]GTTTTTTTTTTACCCCTCCTTAGCT |
| 79 | 2108344 | rs28472590 | [−/GG] | 3 | TGCCCCCCTGTTACATGGGGGGGGG[−/GG]TTTAATTTGGTTTCTGAGCGCATAA |
| 80 | 2108288 | rs58312807 | [C/T] | 3 | GAGTCCTCGGGGCCGTGCACTGATG[C/T]GGGGAGTGTGGGAAGTCTGGCGGTT |
| 81 | 2107971 | rs60649995 | [G/A] | 3 | AGGCTGGCCGGAGGGGAAGGGGCTA[G/A]CAGGTGTGTAAACAGAGGGTTCCAT |
| 82 | 2107909 | rs58562468 | [A/G] | 3 | CAGGGTGGCCGCCTTCCGCACACTTG[A/G]GGAACCCTCCCCTCTCCCTCGGTGA |
| 83 | 2107900 | rs1065687 | [C/G] | 3 | CGCCTTCCGCACACTTGAGGAACCCT[C/G]CCCTCTCCCTCGGTGACATCTTGCC |
| 84 | 2109167 | rs3208122 | [A/C] | 2 | TAAGCAACTACGATATCTGTATGGAT[A/C]AGGCCAAAGTCCCGCTAAGATTCTC |
| 85 | 2109117 | rs3168310 | [C/G] | 2 | CCAATGTTTTCATGGTCTGAGCCCC[C/G]CTCCTGTTCCCATCTCCACTGCCCC |

TABLE 1B-continued

Known Polymorphisms in IGF2 exon 9.

| Seq. ID | Genomic Position* | dbSNP | Alleles | Block | Sequence |
|---|---|---|---|---|---|
| 86 | 2108911 | rs58527086 | [–/T] | 3 | CATCGTGGCTCACGCTGCGGGGGCCG[–/T]GGGGACAGGCGCCAAGGAGGCCAGC |
| 87 | 2108682 | rs57156844 | [C/T] | 3 | ACATTTCTTGGGGGGTCCCCAGGAGA[C/T]GGGCAAAGATGATCCCTAGGTGTGC |
| 88 | 2108628 | rs3802971 | [C/T] | 3 | AGTCCTCGGGGCCGTGCACTGATG[C/T]GGGGAGTGTGGGAAGTCTGGCGGTT |
| 89 | 2108395 | rs3180700 | [T/G] | 3 | GCATTTTTCCTTTTTTTTTTTTTT[T/G]GTTTTTTTTTTACCCCTCCTTAGCT |
| 90 | 2108344 | rs57423851 | [–/GG] | 3 | TGCCCCCCTGTTACATGGGGGGGGG[–/GG]TTTAATTTGGTTTCTGAGCGCATAA |
| 91 | 2108288 | rs35818489 | [C/T] | 3 | GAGTCCTCGGGGCCGTGCACTGATG[C/T]GGGGAGTGTGGGAAGTCTGGCGGTT |
| 92 | 2107971 | rs11825733 | [G/A] | 3 | AGGCTGGCCGGAGGGGAAGGGGCTA[G/A]CAGGTGTGTAAACAGAGGGTTCCAT |
| 93 | 2107909 | rs11541377 | [A/G] | 3 | CAGGGTGGCCGCCTTCCGCACACTTG[A/G]GGAACCCTCCCCTCTCCCTCGGTGA |
| 94 | 2107900 | rs11541375 | [C/G] | 3 | CGCCTTCCGCACACTTGAGGAACCCT[C/G]CCCTCTCCCTCGGTGACATCTTGCC |
| 95 | 2107862 | rs11541373 | [C/T] | 3 | GGTGACATCTTGCCCGCCCCTCAGCA[C/T]CCTGCCTTGTCTCCAGGAGGTCCGA |
| 96 | 2107847 | rs11541372 | [A/C] | 3 | CCCCTCAGCACCCTGCCTTGTCTCC[A/C]GGAGGTCCGAAGCTCTGTGGGACCT |
| 97 | 2107755 | rs11541374 | [G/T] | 3 | CAGGCGGGTCTGAGCCCACAGAGCAG[G/T]AGAGCTGCCAGGTCTGCCCATCGAC |
| 98 | 2107602 | rs3189464 | [A/C] | 3 | CCTCGCCCCCACTTGTGCCCCAGCT[A/C]AGCCCCCCTGCACGCAGCCCGACTA |
| 99 | 2107472 | rs61745040 | [C/T] | 3 | CAGTCGCAGAGGGTCCCTCGGCAAG[C/T]GCCCTGTGAGTGGGCCATTCGGAAC |
| 100 | 2107471 | rs11564732 | [G/A/T] | 3 | AGTCGCAGAGGGTCCCTCGGCAAGC[G/A/T]CCCTGTGAGTGGGCCATTCGGAACA |

*Coordinates relative to NCBI Build 36, Chr: 11

TABLE 1C

Known Polymorphisms in IGF2 exon 9.

| Seq. ID | Genomic Position* | dbSNP | Alleles | Block | Sequence |
|---|---|---|---|---|---|
| 101 | 2107452 | rs11541376 | [C/T] | 3 | GCAAGCGCCCTGTGAGTGGGCCATT[C/T]GGAACATTGGACAGAAGCCCAAAGA |
| 102 | 2107273 | rs7873 | [A/G] | 3 | GTGTTCCCGGGGGCACTTGCCGACC[A/G]GCCCCTTGCGTCCCCAGGTTTGCAG |
| 103 | 2107263 | rs61745039 | [G/A/T] | 3 | GGGCACTTGCCGACCAGCCCCTTGC[G/A/T]TCCCCAGGTTTGCAGCTCTCCCCTG |
| 104 | 2107147 | rs3177805 | [C/T] | 3 | TTGTCTCCTCCCCGTGTCCCCAATGT[C/T]TTCAGTGGGGGCCCCCTCTTGGGT |
| 105 | 2107135 | rs1065715 | [C/G] | 3 | CGTGTCCCCAATGTCTTCAGTGGGG[C/G]CCCCCTCTTGGGTCCCCTCCTCTGC |
| 106 | 2107134 | rs11541371 | [C/G] | 3 | TGTCCCCAATGTCTTCAGTGGGGGG[C/G]CCCCTCTTGGGTCCCCTCCTCTGCC |
| 107 | 2107128 | rs1049926 | [C/T] | 3 | CCAATGTCTTCAGTGGGGGGCCCCCT[C/T]TTGGGTCCCCTCCTCTGCCATCACC |
| 108 | 2107113 | rs3177946 | [C/T] | 3 | GGGGCCCCCTCTTGGGTCCCCTCCT[C/T]TGCCATCACCTGAAGACCCCCACGC |
| 109 | 2107049 | rs1050035 | [A/C] | 3 | GTCACCTGTGCCTGCCGCCTCGGTCC[A/C]CCTTGCGGCCCGTGTTTGACTCAAC |
| 110 | 2107027 | rs11541370 | [A/G] | 3 | AATATTAGCGTTAAAGGAGCTGAGTT[A/G]AGTCAAACACGGGCCGCAAGGTGGA |
| 111 | 2107020 | rs2585 | [G/A/C/T] | 3 | TGCGGCCCGTGTTTGACTCAACTCA[G/A/C/T]CTCCTTTAACGCTAATATTTCCGGC |
| 112 | 2106955 | rs1050141 | [C/A] | 3 | GGGTTTTGTCTTTAACCTTGTAACG[C/A]TTGCAATCCCAATAAAGCATTAAAA |

*Coordinates relative to NCBI Build 36, Chr: 11

TABLE 2A

Novel Polymorphisms in IGF2 exon 9.

| Seq. ID | Genomic Position* | Alleles | Block | Sequence |
|---|---|---|---|---|
| 1 | 2110869 | [G/A] | 1 | GCGTTCAGGGAGGCCAAACGTCACC[G/A]TCCCCTGATTGCTCTACCCACCCAA |
| 2 | 2110827 | [G/A] | 1 | CCCACCCAAGACCCCGCCCACGGGG[G/A]CGCCCCCCCAGAGATGGCCAGCAAT |
| 3 | 2110825 | [G/A] | 1 | CACCCAAGACCCCGCCCACGGGGGC[G/A]CCCCCCCAGAGATGGCCAGCAATCG |
| 4 | 2110781 | [G/A] | 1 | GCAATCGGAAGTGAGCAAAACTGCC[G/A]CAAGTCTGCAGCCCGGCGCCACCAT |
| 5 | 2110657 | [G/A] | 1 | TGGGGCTTCTCCTGACCCAGTCCCC[G/A]TGCCCCGCCTCCCCGAAACAGGCTA |
| 6 | 2110465 | [C/T] | 1 | TTAAACTAACCCCCTTCCCCCCCCC[C/T]CACAACAACCCTCTTAAAACTAATT |
| 7 | 2110430 | [G/A/T] | 1 | CCTCTTAAAACTAATTGGCTTTTTA[G/A/T]AAACACCCCACAAAAGCTCAGAAAT |
| 8 | 2110287 | [C/G] | 1 | AAGGAATTTGGCACTCCCCACCCCC[C/G]TCTTTCTCTTCTCCCTTGGACTTTG |
| 9 | 2110197 | [C/T] | 2 | GAGAAAAGAAGGACCCCAGAAATCA[C/T]AGGTGGGCACGTCGCTGCTACCGCC |
| 10 | 2110187 | [C/T] | 2 | GGACCCCAGAAATCACAGGTGGGCA[C/T]GTCGCTGCTACCGCCATCTCCCTTC |
| 11 | 2110129 | [G/A] | 2 | AATTTTCAGGGTAAACTGGCCATCC[G/A]AAAATAGCAACAACCCAGACTGGCT |
| 12 | 2110109 | [C/T] | 2 | CATCCGAAAATAGCAACAACCCAGA[C/T]TGGCTCCTCACTCCCTTTTCCATCA |
| 13 | 2110063 | [A/C] | 2 | CATCACTAAAAATCACAGAGCAGTC[A/C]GAGGGACCCAGTAAGACCAAAGGAG |
| 14 | 2110060 | [G/C] | 2 | CACTAAAAATCACAGAGCAGTCAGA[G/C]GGACCCAGTAAGACCAAAGGAGGGG |
| 15 | 2110058 | [G/T/A] | 2 | CTAAAAATCACAGAGCAGTCAGAGG[G/T/A]ACCCAGTAAGACCAAAGGAGGGGAG |
| 16 | 2109220 | [A/C] | 2 | GCGCACACACACGCACACCCCCACA[A/C]AATTGGATGAAAACAATAAGCATAT |
| 17 | 2109153 | [G/A] | 2 | TCTGTATGGATCAGGCCAAAGTCCC[G/A]CTAAGATTCTCCAATGTTTTCATGG |
| 18 | 2109095 | [C/T] | 3 | CCCGCTCCTGTTCCCATCTCCACTG[C/T]CCCTCGGCCCTGTCTGTGCCCTGCC |
| 19 | 2109074 | [C/G] | 3 | ACTGCCCCTCGGCCCTGTCTGTGCC[C/G]TGCCTCTCAGAGGAGGGGCTCAGA |
| 20 | 2108843 | [T/C] | 3 | CATTCCCGATACACCTTACTTACTG[T/C]GTGTTGGCCCAGCCAGAGTGAGGAA |
| 21 | 2108835 | [C/T] | 3 | ATACACCTTACTTACTGTGTGTTGG[C/T]CCAGCCAGAGTGAGGAAGGAGTTTG |
| 22 | 2108806 | [A/C/T] | 3 | GCCAGAGTGAGGAAGGAGTTTGGCC[A/C/T]CATTGGAGATGGCGGTAGCTGAGCA |
| 23 | 2108738 | [G/A/T] | 3 | AGCCTGACTCCCTGGTGTGCTCCTG[G/A/T]AAGGAAGATCTTGGGGACCCCCCCA |
| 24 | 2108440 | [C/T/G] | 3 | CAAATTTCATGTCAATTGATCTATT[C/T/G]CCCCTCTTTGTTTCTTGGGGCATTT |
| 25 | 2108424 | [T/G] | 3 | TGATCTATTCCCCCTCTTTGTTTCT[T/G]GGGGCATTTTTCCTTTTTTTTTTTT |
| 26 | 2108417 | [T/G] | 3 | TTCCCCCTCTTTGTTTCTTGGGGCA[T/G]TTTTCCTTTTTTTTTTTTTTGTT |
| 27 | 2108326 | [G/A] | 3 | AATTAAACCCCCCCCCCATGTAACA[G/A]GGGGGCAGTGACAAAAGCAAGAACG |
| 28 | 2107988 | [C/T/A] | 3 | GGCTCCTGGCTGGCCTGAGGCTGGC[C/T/A]GGAGGGGAAGGGGCTAGCAGGTGTG |
| 29 | 2107918 | [G/C/A] | 3 | GGCTGGGGCAGGGTGGCCGCCTTCC[G/C/A]CACACTTGAGGAACCCTCCCCTCTC |

*Coordinates relative to NCBI Build 36, Chr: 11

TABLE 2B

Novel Polymorphisms in IGF2 exon 9.

| Seq. ID | Genomic Position* | Alleles | Block | Sequence |
|---|---|---|---|---|
| 30 | 2107819 | [T/G] | 3 | AGGTCCGAAGCTCTGTGGGACCTCT[T/G]GGGGGCAAGGTGGGGTGAGGCCGGG |
| 31 | 2107776 | [G/A] | 3 | AGGCCGGGGAGTAGGGAGGTCAGGC[G/A]GGTCTGAGCCCACAGAGCAGGAGAG |
| 32 | 2107668 | [G/A] | 3 | ATGCCATAGCAGCCACCACCGCGGC[G/A]CCTAGGGCTGCGGCAGGGACTCGGC |

TABLE 2B-continued

Novel Polymorphisms in IGF2 exon 9.

| Seq. ID | Genomic Position* | Alleles | Block | Sequence |
|---|---|---|---|---|
| 33 | 2107664 | [A/T] | 3 | CATAGCAGCCACCACCGCGGCGCCT[A/T]GGGCTGCGGCAGGGACTCGGCCTCT |
| 34 | 2107625 | [C/T] | 3 | GACTCGGCCTCTGGGAGGTTTACCT[C/T]GCCCCCACTTGTGCCCCCAGCTCAG |
| 35 | 2107595 | [C/G] | 3 | CCACTTGTGCCCCCAGCTCAGCCCC[C/G]CTGCACGCAGCCCGACTAGCAGTCT |
| 36 | 2107523 | [C/T] | 3 | CCTGGTGACGGGGCTGGCATGACCC[C/T]GGGGGTCGTCCATGCCAGTCCGCCT |
| 37 | 2107478 | [G/A] | 3 | CCGCCTCAGTCGCAGAGGGTCCCTC[G/A]GCAAGCGCCCTGTGAGTGGGCCATT |
| 38 | 2107472 | [C/T] | 3 | CAGTCGCAGAGGGTCCCTCGGCAAG[C/T]GCCCTGTGAGTGGGCCATTCGGAAC |
| 39 | 2107469 | [C/T] | 3 | TCGCAGAGGGTCCCTCGGCAAGCGC[C/T]CTGTGAGTGGGCCATTCGGAACATT |
| 40 | 2107379 | [C/T] | 3 | ACCCACATTGGCCTGAGATCCAAAA[C/T]GCTTCGAGGCACCCCAAATTACCTG |
| 41 | 2107353 | [C/G] | 3 | GCTTCGAGGCACCCCAAATTACCTG[C/G]CCATTCGTCAGGACACCCACCCACC |
| 42 | 2107278 | [C/T] | 3 | AGTGGGTGTTCCCGGGGGCACTTGC[C/T]GACCAGCCCCTTGCGTCCCCAGGTT |
| 43 | 2107263 | [G/A] | 3 | GGGCACTTGCCGACCAGCCCCTTGC[G/A]TCCCCAGGTTTGCAGCTCTCCCCTG |
| 44 | 2107151 | [A/G] | 3 | ATCTTGTCTCCTCCCCGTGTCCCCA[A/G]TGTCTTCAGTGGGGGCCCCCTCTT |
| 45 | 2107054 | [G/A] | 3 | GAATGTCACCTGTGCCTGCCGCCTC[G/A]GTCCACCTTGCGGCCCGTGTTTGAC |
| 46 | 2107037 | [G/A] | 3 | GCCGCCTCGGTCCACCTTGCGGCCC[G/A]TGTTTGACTCAACTCAACTCCTTTA |
| 47 | 2106956 | [G/A/C] | 3 | TGGGTTTTGTCTTTAACCTTGTAAC[G/A/C]CTTGCAATCCCAATAAAGCATTAAA |

*Coordinates relative to NCBI Build 36, Chr: 11

TABLE 3

Observed Heterozygosity of Transcribed IGF2 SNPs in Human Populations

| SEQ ID NO: | Genomic Position | Block | All ObsHET | AA ObsHET | CAU ObsHET |
|---|---|---|---|---|---|
| 1 | 2110869 | 1 | 1.08% (6 of 553) | 3.3% (3 of 91) | 1% (2 of 201) |
| 4 | 2110781 | 1 | 0.95% (4 of 421) | 2.9% (2 of 69) | 0% (0 of 155) |
| 56 | 2110764 | 1 | 1.45% (1 of 69) | 6.25% (1 of 16) | 0% (0 of 35) |
| 6 | 2110465 | 1 | 3.38% (7 of 207) | 11.48% (7 of 61) | 0% (0 of 51) |
| 7 | 2110430 | 1 | 1.23% (1 of 81) | 16.67% (1 of 6) | 0% (0 of 54) |
| 64 | 2110210 | 2 | 54.46% (110 of 202) | 13.89% (5 of 36) | 63.08% (41 of 65) |
| 10 | 2110187 | 2 | 2.82% (15 of 531) | 17.33% (13 of 75) | 1% (2 of 201) |
| 16 | 2109220 | 2 | 1.57% (9 of 572) | 9.88% (8 of 81) | 0% (0 of 214) |
| 83 | 2109215 | 2 | 3.28% (19 of 579) | 0% (0 of 94) | 8.13% (17 of 209) |
| 85 | 2109117 | 2 | 38.59% (137 of 355) | 27.27% (18 of 66) | 40.16% (49 of 122) |
| 20 | 2108843 | 3 | 0.35% (2 of 566) | 2.3% (2 of 87) | 0% (0 of 202) |
| 21 | 2108835 | 3 | 4.07% (20 of 492) | 1.43% (1 of 70) | 9.94% (18 of 181) |
| 87 | 2108682 | 3 | 1.89% (5 of 265) | 14.29% (4 of 28) | 1.01% (1 of 99) |
| 88 | 2108628 | 3 | 7.57% (14 of 185) | 3.13% (1 of 32) | 4.88% (2 of 41) |
| 25 | 2108424 | 3 | 0.35% (1 of 288) | 2.17% (1 of 46) | 0% (0 of 89) |
| 26 | 2108417 | 3 | 3.38% (9 of 266) | 7.32% (3 of 41) | 6.74% (6 of 89) |
| 92 | 2107971 | 3 | 2.8% (15 of 536) | 16.3% (15 of 92) | 0% (0 of 185) |
| 32 | 2107668 | 3 | 2.35% (12 of 511) | 0% (0 of 94) | 0.7% (1 of 142) |
| 100 | 2107471 | 3 | 4.66% (26 of 558) | 1.05% (1 of 95) | 1.97% (4 of 203) |
| 102 | 2107273 | 3 | 6.41% (32 of 499) | 14.81% (8 of 54) | 9.34% (17 of 182) |
| 111 | 2107020 | 3 | 50.19% (135 of 269) | 23.08% (3 of 13) | 49.58% (59 of 119) |
| 47 | 2106956 | 3 | 0.33% (1 of 304) | 0% (0 of 70) | 0% (0 of 115) |

| SEQ ID NO: | CHI ObsHET | JAP ObsHET | MEX ObsHET |
|---|---|---|---|
| 1 | 0% (0 of 84) | 0% (0 of 90) | 1.15% (1 of 87) |
| 4 | 0% (0 of 61) | 2.86% (2 of 70) | 0% (0 of 66) |
| 56 | 0% (0 of 8) | 0% (0 of 2) | 0% (0 of 8) |
| 6 | 0% (0 of 21) | 0% (0 of 29) | 0% (0 of 45) |
| 7 | 0% (0 of 8) | 0% (0 of 7) | 0% (0 of 6) |
| 64 | 70.83% (17 of 24) | 64.1% (25 of 39) | 57.89% (22 of 38) |

TABLE 3-continued

Observed Heterozygosity of Transcribed IGF2 SNPs in Human Populations

| | | | |
|---|---|---|---|
| 10 | 0% (0 of 80) | 0% (0 of 89) | 0% (0 of 86) |
| 16 | 0% (0 of 90) | 0% (0 of 91) | 1.04% (1 of 96) |
| 83 | 0% (0 of 90) | 0% (0 of 91) | 2.11% (2 of 95) |
| 85 | 40.74% (22 of 54) | 53.85% (35 of 65) | 27.08% (13 of 48) |
| 20 | 0% (0 of 90) | 0% (0 of 91) | 0% (0 of 96) |
| 21 | 0% (0 of 79) | 0% (0 of 81) | 1.23% (1 of 81) |
| 87 | 0% (0 of 41) | 0% (0 of 52) | 0% (0 of 45) |
| 88 | 12.2% (5 of 41) | 20% (5 of 25) | 2.17% (1 of 46) |
| 25 | 0% (0 of 67) | 0% (0 of 57) | 0% (0 of 29) |
| 26 | 0% (0 of 44) | 0% (0 of 56) | 0% (0 of 36) |
| 92 | 0% (0 of 79) | 0% (0 of 87) | 0% (0 of 93) |
| 32 | 10.23% (9 of 88) | 2.2% (2 of 91) | 0% (0 of 96) |
| 100 | 1.16% (1 of 86) | 5.75% (5 of 87) | 17.24% (15 of 87) |
| 102 | 0% (0 of 86) | 0% (0 of 85) | 7.61% (7 of 92) |
| 111 | 50% (24 of 48) | 53.85% (21 of 39) | 56% (28 of 50) |
| 47 | 0% (0 of 43) | 0% (0 of 42) | 2.94% (1 of 34) |

\* Coordinates relative to NCBI Build 36, Chr: 11

TABLE 4

Informative SNPs in Chinese

| SEQ ID NO: | Genomic Position | Block | Obs Het |
|---|---|---|---|
| 64 | 2110210 | 2 | 70.83% (17 of 24) |
| 85 | 2109117 | 2 | 40.74% (22 of 54) |
| 88 | 2108628 | 3 | 12.2% (5 of 41) |
| 32 | 2107668 | 3 | 10.23% (9 of 88) |
| 111 | 2107020 | 3 | 50% (24 of 48) |

TABLE 5

Informative SNPs in Japanese

| SEQ ID NO: | Genomic Position | Block | Obs Het |
|---|---|---|---|
| 4 | 2110781 | 1 | 2.86% (2 of 70) |
| 64 | 2110210 | 2 | 64.1% (25 of 39) |
| 85 | 2109117 | 2 | 53.85% (35 of 65) |
| 88 | 2108628 | 3 | 20% (5 of 25) |
| 32 | 2107668 | 3 | 2.2% (2 of 91) |
| 100 | 2107471 | 3 | 5.75% (5 of 87) |
| 111 | 2107020 | 3 | 53.85% (21 of 39) |

TABLE 6

Inf. SNPs in African Amer.

| SEQ ID NO: | Genomic Position | Block | Obs Het |
|---|---|---|---|
| 1 | 2110869 | 1 | 3.3% (3 of 91) |
| 4 | 2110781 | 1 | 2.9% (2 of 69) |
| 56 | 2110764 | 1 | 6.25% (1 of 16) |
| 6 | 2110465 | 1 | 11.48% (7 of 61) |
| 7 | 2110430 | 1 | 16.67% (1 of 6) |
| 64 | 2110210 | 2 | 13.89% (5 of 36) |
| 10 | 2110187 | 2 | 17.33% (13 of 75) |
| 16 | 2109220 | 2 | 9.88% (8 of 81) |
| 85 | 2109117 | 2 | 27.27% (18 of 66) |
| 20 | 2108843 | 3 | 2.3% (2 of 87) |
| 87 | 2108682 | 3 | 14.29% (4 of 28) |
| 88 | 2108628 | 3 | 3.13% (1 of 32) |
| 25 | 2108424 | 3 | 2.17% (1 of 46) |
| 26 | 2108417 | 3 | 7.32% (3 of 41) |
| 92 | 2107971 | 3 | 16.3% (15 of 92) |
| 102 | 2107273 | 3 | 14.81% (8 of 54) |
| 111 | 2107020 | 3 | 23.08% (3 of 13) |

TABLE 7

Informative SNPs in Caucasian

| SEQ | Genomic | Block | Obs Het |
|---|---|---|---|
| 64 | 2110210 | 2 | 63.08% (41 of 65) |
| 83 | 2109215 | 2 | 8.13% (17 of 209) |
| 85 | 2109117 | 2 | 40.16% (49 of 122) |
| 21 | 2108835 | 3 | 9.94% (18 of 181) |
| 88 | 2108628 | 3 | 4.88% (2 of 41) |
| 26 | 2108417 | 3 | 6.74% (6 of 89) |
| 100 | 2107471 | 3 | 1.97% (4 of 203) |
| 102 | 2107273 | 3 | 9.34% (17 of 182) |
| 111 | 2107020 | 3 | 49.58% (59 of 119) |

TABLE 8

Informative SNPs in Mexicans

| SEQ ID | Genomic | Block | Obs Het |
|---|---|---|---|
| 64 | 2110210 | 2 | 57.89% (22 of 38) |
| 83 | 2109215 | 2 | 2.11% (2 of 95) |
| 85 | 2109117 | 2 | 27.08% (13 of 48) |
| 88 | 2108628 | 3 | 2.17% (1 of 46) |
| 100 | 2107471 | 3 | 17.24% (15 of 87) |
| 102 | 2107273 | 3 | 7.61% (7 of 92) |
| 111 | 2107020 | 3 | 56% (28 of 50) |
| 47 | 2106956 | 3 | 2.94% (1 of 34) |

What is claimed is:

1. A method of quantifying allelic-specific expression of RNA in a human individual that is a heterozygote for a single nucleotide polymorphism (SNP) in the Insulin Growth Factor-2 (IGF2) gene, the method comprising
   quantifying in a sample from the individual the amount of RNA comprising each polymorphic option of the SNP, wherein the SNP comprises SEQ ID NO: 10.

2. The method of claim 1, wherein the sample is a blood, stool, or tissue sample.

3. The method of claim 1, wherein the RNA is reverse transcribed into cDNA and the quantity of allele-specific cDNA is used to determine the amount of RNA.

4. The method of claim 1, further comprising determining that the individual is heterozygous for the SNP.

* * * * *

UNITED STATES PATENT AND TRADEMARK OFFICE
CERTIFICATE OF CORRECTION

PATENT NO. : 8,420,315 B2  Page 1 of 1
APPLICATION NO. : 12/672066
DATED : April 16, 2013
INVENTOR(S) : Jared Ordway et al.

It is certified that error appears in the above-identified patent and that said Letters Patent is hereby corrected as shown below:

<u>In the specification:</u>

Column 1, line 63, replace "LOT" with --LOI--

Column 2, line 45, replace "LOT" with --LOI--

Column 3, line 1, replace "LOT" with --LOI--

Column 3, line 6, replace "LOT" with --LOI--

Column 10, line 40, replace "LOT" with --LOI--

Column 11, line 26, replace "LOT" with --LOI--

Column 26, line 17, replace "LOT" with --LOI--

Column 30, line 61, replace "LOT" with --LOI--

Column 31, line 21, replace "LOT" with --LOI--

Signed and Sealed this
Thirteenth Day of August, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,420,315 B2 | Page 1 of 1 |
| APPLICATION NO. | : 12/672066 | |
| DATED | : April 16, 2013 | |
| INVENTOR(S) | : Ordway et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 449 days.

Signed and Sealed this
Fourth Day of November, 2014

Michelle K. Lee
*Deputy Director of the United States Patent and Trademark Office*

SEQUENCE LISTING

<160> NUMBER OF SEQ ID NOS: 116

<210> SEQ ID NO 1
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 1
gcgttcaggg aggccaaacg tcaccrtccc ctgattgctc tacccaccca a        51

<210> SEQ ID NO 2
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 2
cccacccaag accccgccca cggggdcgcc ccccagaga tggccagcaa t         51

<210> SEQ ID NO 3
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 3
cacccaagac cccgcccacg ggggcrcccc cccagagatg ccagcaatc g         51

<210> SEQ ID NO 4
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 4
gcaatcggaa gtgagcaaaa ctgccrcaag tctgcagccc ggcgccacca t        51

<210> SEQ ID NO 5
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 5
tggggcttct cctgacccag tccccrtgcc ccgcctcccc gaaacaggct a        51

<210> SEQ ID NO 6
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

```
<400> SEQUENCE: 6
ttaaactaac cccctteccc ccccchcaca acaaccetet taaaactaat t            51

<210> SEQ ID NO 7
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 7
cctcttaaaa ctaattggct ttttadaaac accccacaaa agctcagaaa t            51

<210> SEQ ID NO 8
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 8
aaggaatttg gcactcccca cccccstctt tctcttctcc cttggacttt g            51

<210> SEQ ID NO 9
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 9
gagaaaagaa ggaccccaga aatcayaggt gggcacgtcg ctgctaccgc c            51

<210> SEQ ID NO 10
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 10
ggaccccaga aatcacaggt gggcaygtcg ctgctaccgc catctccctt c            51

<210> SEQ ID NO 11
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 11
aattttcagg gtaaactggc catccraaaa tagcaacaac ccagactggc t            51

<210> SEQ ID NO 12
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 12
```

```
catccgaaaa tagcaacaac ccagaytggc tcctcactcc cttttccatc a            51
```

<210> SEQ ID NO 13
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 13

```
catcactaaa aatcacagag cagtchgagg gacccagtaa gaccaaagga g            51
```

<210> SEQ ID NO 14
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 14

```
cactaaaaat cacagagcag tcagasggac ccagtaagac caaaggaggg g            51
```

<210> SEQ ID NO 15
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 15

```
ctaaaaatca cagagcagtc agaggdaccc agtaagacca aaggagggga g            51
```

<210> SEQ ID NO 16
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 16

```
gcgcacacac acgcacaccc ccacamaatt ggatgaaaac aataagcata t            51
```

<210> SEQ ID NO 17
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 17

```
tctgtatgga tcaggccaaa gtcccvctaa gattctccaa tgttttcatg g            51
```

<210> SEQ ID NO 18
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 18

```
cccgctcctg ttcccatctc cactgyccct cggccctgtc tgtgccctgc c            51
```

<210> SEQ ID NO 19
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 19
actgcccctc ggccctgtct gtgccstgcc tctcagagga gggggctcag a         51

<210> SEQ ID NO 20
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 20
cattcccgat acaccttact tactgygtgt tggcccagcc agagtgagga a         51

<210> SEQ ID NO 21
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 21
atacacctta cttactgtgt gttggyccag ccagagtgag gaaggagttt g         51

<210> SEQ ID NO 22
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 22
gccagagtga ggaaggagtt tggcchcatt ggagatggcg gtagctgagc a         51

<210> SEQ ID NO 23
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 23
agcctgactc cctggtgtgc tcctgdaagg aagatcttgg ggacccccccc a         51

<210> SEQ ID NO 24
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 24
caaatttcat gtcaattgat ctattbcccc tctttgtttc ttggggcatt t         51

<210> SEQ ID NO 25
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 25
tgatctattc cccctctttg tttctkgggg catttttcct tttttttttt t         51

<210> SEQ ID NO 26
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 26 ttcccctct ttgtttcttg gggcadtttt ccttttttt ttttttttgt t            51

<210> SEQ ID NO 27
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 27
aattaaaccc ccccccatg taacargggg gcagtgacaa aagcaagaac g           51

<210> SEQ ID NO 28
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 28
ggctcctggc tggcctgagg ctggchggag gggaaggggc tagcaggtgt g         51

<210> SEQ ID NO 29
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 29
ggctggggca gggtggccgc cttccvcaca cttgaggaac cctcccctct c         51

<210> SEQ ID NO 30
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 30
aggtccgaag ctctgtggga cctctkgggg gcaaggtggg gtgaggccgg g    51

<210> SEQ ID NO 31
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 31
aggccgggga gtagggaggt caggcrggtc tgagcccaca gagcaggaga g    51

<210> SEQ ID NO 32
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 32
atgccatagc agccaccacc gcggcrccta gggctgcggc agggactcgg c    51

<210> SEQ ID NO 33
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 33
catagcagcc accacgcgg cgcctwgggc tgcggcaggg actcggcctc t    51

<210> SEQ ID NO 34
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 34
gactcggcct ctgggaggtt tacctygccc ccacttgtgc ccccagctca g    51

<210> SEQ ID NO 35
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 35
ccacttgtgc ccccagctca gccccsctgc acgcagcccg actagcagtc t    51

<210> SEQ ID NO 36
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 36
cctggtgacg gggctggcat gacccygggg gtcgtccatg ccagtccgcc t    51

```
<210> SEQ ID NO 37
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9
<220> FEATURE:
<221> NAME/KEY: modified_base
<222> LOCATION: (26)...(26)
<223> OTHER INFORMATION: n = g, a, c or t

<400> SEQUENCE: 37
ccgcctcagt cgcagagggt ccctcngcaa gcgccctgtg agtgggccat t            51

<210> SEQ ID NO 38
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 38
cagtcgcaga gggtccctcg gcaagygccc tgtgagtggg ccattcggaa c            51

<210> SEQ ID NO 39
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 39
tcgcagaggg tccctcggca agcgcbctgt gagtgggcca ttcggaacat t            51

<210> SEQ ID NO 40
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 40
acccacattg gcctgagatc caaaaygctt cgaggcaccc caaattacct g            51

<210> SEQ ID NO 41
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 41
gcttcgaggc accccaaatt acctgsccat tcgtcaggac acccacccac c            51

<210> SEQ ID NO 42
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 42
```
agtgggtgtt cccgggggca cttgcygacc agccccttgc gtccccaggt t        51

<210> SEQ ID NO 43
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 43
gggcacttgc cgaccagccc cttgcdtccc caggtttgca gctctcccct g        51

<210> SEQ ID NO 44
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 44
atcttgtctc ctccccgtgt ccccartgtc ttcagtgggg ggcccctct t         51

<210> SEQ ID NO 45
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 45
gaatgtcacc tgtgcctgcc gcctcrgtcc accttgcggc ccgtgtttga c        51

<210> SEQ ID NO 46
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9

<400> SEQUENCE: 46
gccgcctcgg tccaccttgc ggcccrtgtt tgactcaact caactccttt a        51

<210> SEQ ID NO 47
<211> LENGTH: 51
<212> TYPE: DNA
<213> ORGANISM: Artificial Sequence
<220> FEATURE:
<223> OTHER INFORMATION: novel single nucleotide polymorphism (SNP) in
      human insulin growth factor-2 (IGF2) gene exon 9
<220> FEATURE:
<221> NAME/KEY: modified_base
<222> LOCATION: (26)...(26)
<223> OTHER INFORMATION: n = g, a, c or t

<400> SEQUENCE: 47
tgggttttgt ctttaacctt gtaacncttg caatcccaat aaagcattaa a        51

<210> SEQ ID NO 48
<211> LENGTH: 52
<212> TYPE: DNA
<213> ORGANISM: Artificial Sequence
<220> FEATURE:
<223> OTHER INFORMATION: known single nucleotide polymorphism (SNP)
      rs1803647 in human insulin growth factor-2 (IGF2)

```
gene

<400> SEQUENCE: 48
tgctgtttcc gcagctgtga cctggcsctc ctggagacgt actgtgctac cc            52

<210> SEQ ID NO 49
<211> LENGTH: 51
<212> TYPE: DNA
<213> ORGANISM: Artificial Sequence
<220> FEATURE:
<223> OTHER INFORMATION: known single nucleotide polymorphism (SNP)
      rs14367 in human insulin growth factor-2 (IGF2) gene

<400> SEQUENCE: 49
agttcttcca atatgacacc tggaarcagt ccacccagcg cctgcgcagg g             51

<210> SEQ ID NO 50
<211> LENGTH: 51
<212> TYPE: DNA
<213> ORGANISM: Artificial Sequence
<220> FEATURE:
<223> OTHER INFORMATION: known single nucleotide polymorphism (SNP)
      rs1065443 in human insulin growth factor-2 (IGF2)
      gene

<400> SEQUENCE: 50
ggaagcagtc cacccagcgc ctgcgyaggg gcctgcctgc cctcctgcgt g             51

<210> SEQ ID NO 51
<211> LENGTH: 52
<212> TYPE: DNA
<213> ORGANISM: Artificial Sequence
<220> FEATURE:
<223> OTHER INFORMATION: known single nucleotide polymorphism (SNP)
      rs11545014 in human insulin growth factor-2 (IGF2)
      gene

<400> SEQUENCE: 51
aagaccccgc ccacgggggc gcccccycag agatggccag caatcggaag tg            52

<210> SEQ ID NO 52
<211> LENGTH: 52
<212> TYPE: DNA
<213> ORGANISM: Artificial Sequence
<220> FEATURE:
<223> OTHER INFORMATION: known single nucleotide polymorphism (SNP)
      rs1050342 in human insulin growth factor-2 (IGF2)
      gene

<400> SEQUENCE: 52
agaccccgcc cacgggggcg cccccmaga gatggccagc aatcggaagt ga             52

<210> SEQ ID NO 53
<211> LENGTH: 52
<212> TYPE: DNA
<213> ORGANISM: Artificial Sequence
<220> FEATURE:
<223> OTHER INFORMATION: known single nucleotide polymorphism (SNP)
      rs12993 in human insulin growth factor-2 (IGF2) gene

<400> SEQUENCE: 53
cccccagaga tggccagcaa tcggaaktga gcaaaactgc cgcragtctg ca            52

<210> SEQ ID NO 54
<211> LENGTH: 52
<212> TYPE: DNA
<213> ORGANISM: Artificial Sequence
<220> FEATURE:
```

<223> OTHER INFORMATION: known single nucleotide polymorphism (SNP)
     rs9282726 in human insulin growth factor-2 (IGF2)
     gene

<400> SEQUENCE: 54
caatcggaak tgagcaaaac tgccgcragt ctgcagccyg gygccaccat cc        52

<210> SEQ ID NO 55
<211> LENGTH: 52
<212> TYPE: DNA
<213> ORGANISM: Artificial Sequence
<220> FEATURE:
<223> OTHER INFORMATION: known single nucleotide polymorphism (SNP)
     rs3741214 in human insulin growth factor-2 (IGF2)
     gene

<400> SEQUENCE: 55
agcaaaactg ccgcaagtct gcagccyggc gccaccatcc tgcagcctcc tc        52

<210> SEQ ID NO 56
<211> LENGTH: 51
<212> TYPE: DNA
<213> ORGANISM: Artificial Sequence
<220> FEATURE:
<223> OTHER INFORMATION: known single nucleotide polymorphism (SNP)
     rs2230949 in human insulin growth factor-2 (IGF2)
     gene

<400> SEQUENCE: 56
aaactgccgc aagtctgcag cccggygcca ccatcctgca gcctcctcct g         51

<210> SEQ ID NO 57
<211> LENGTH: 51
<212> TYPE: DNA
<213> ORGANISM: Artificial Sequence
<220> FEATURE:
<223> OTHER INFORMATION: known single nucleotide polymorphism (SNP)
     rs3213234 in human insulin growth factor-2 (IGF2)
     gene

<400> SEQUENCE: 57
catcctgcag cctcctcctg accackgacg tttccatcag gttccatccc g         51

<210> SEQ ID NO 58
<211> LENGTH: 52
<212> TYPE: DNA
<213> ORGANISM: Artificial Sequence
<220> FEATURE:
<223> OTHER INFORMATION: known single nucleotide polymorphism (SNP)
     rs34337549 in human insulin growth factor-2 (IGF2)
     gene
<220> FEATURE:
<221> NAME/KEY: modified_base
<222> LOCATION: (27)...(27)
<223> OTHER INFORMATION: g at position 27 may be present or absent

<400> SEQUENCE: 58
cggggactgg gtcaggagaa gccccagggg gacgtggaac cgagagattt tc        52

<210> SEQ ID NO 59
<211> LENGTH: 51
<212> TYPE: DNA
<213> ORGANISM: Artificial Sequence
<220> FEATURE:
<223> OTHER INFORMATION: known single nucleotide polymorphism (SNP)
     rs6223 in human insulin growth factor-2 (IGF2) gene

<400> SEQUENCE: 59
caggctactc tcctcggccc cctccmtcgg gctgaggaag cacagcagca t         51

<210> SEQ ID NO 60
<211> LENGTH: 52
<212> TYPE: DNA
<213> ORGANISM: Artificial Sequence
<220> FEATURE:
<223> OTHER INFORMATION: known single nucleotide polymorphism (SNP)
    rs11510 in human insulin growth factor-2 (IGF2) gene

<400> SEQUENCE: 60
tcgggctgag gaagcacagc agcatcwtca aacatgtaca aaatcgattg gc          52

<210> SEQ ID NO 61
<211> LENGTH: 51
<212> TYPE: DNA
<213> ORGANISM: Artificial Sequence
<220> FEATURE:
<223> OTHER INFORMATION: known single nucleotide polymorphism (SNP)
    rs1803648 in human insulin growth factor-2 (IGF2)
    gene

<400> SEQUENCE: 61
atgtacaaaa tcgattggct ttaaamaccc ttcacatacc ctcccccaa a             51

<210> SEQ ID NO 62
<211> LENGTH: 53
<212> TYPE: DNA
<213> ORGANISM: Artificial Sequence
<220> FEATURE:
<223> OTHER INFORMATION: known single nucleotide polymorphism (SNP)
    rs11564731 in human insulin growth factor-2 (IGF2)
    gene
<220> FEATURE:
<221> NAME/KEY: modified_base
<222> LOCATION: (7)...(8)
<223> OTHER INFORMATION: ac at positions 7 and 8 may be present or
    absent

<400> SEQUENCE: 62
aaaacattaa actaaccccc ttccccaccc ccccacaac aaccctctta aaa           53

<210> SEQ ID NO 63
<211> LENGTH: 51
<212> TYPE: DNA
<213> ORGANISM: Artificial Sequence
<220> FEATURE:
<223> OTHER INFORMATION: known single nucleotide polymorphism (SNP)
    rs15737 in human insulin growth factor-2 (IGF2) gene

<400> SEQUENCE: 63
tggcactccc caccccctc tttctyttct cccttggact ttgagtcaaa t             51

<210> SEQ ID NO 64
<211> LENGTH: 51
<212> TYPE: DNA
<213> ORGANISM: Artificial Sequence
<220> FEATURE:
<223> OTHER INFORMATION: known single nucleotide polymorphism (SNP)
    rs680 in human insulin growth factor-2 (IGF2) gene
<220> FEATURE:
<221> NAME/KEY: modified_base
<222> LOCATION: (26)...(26)
<223> OTHER INFORMATION: n = g, a, c or t

<400> SEQUENCE: 64
ctgaaccagc aaagagaaaa gaaggncccc agaaatcaca ggtgggcacg t            51

<210> SEQ ID NO 65
<211> LENGTH: 52

```
<212> TYPE: DNA
<213> ORGANISM: Artificial Sequence
<220> FEATURE:
<223> OTHER INFORMATION: known single nucleotide polymorphism (SNP)
      rs1065685 in human insulin growth factor-2 (IGF2)
      gene

<400> SEQUENCE: 65
cagaaatcac aggtgggcac gtcgctscta ccgccatctc ccttctcacg gg          52

<210> SEQ ID NO 66
<211> LENGTH: 52
<212> TYPE: DNA
<213> ORGANISM: Artificial Sequence
<220> FEATURE:
<223> OTHER INFORMATION: known single nucleotide polymorphism (SNP)
      rs56731553 in human insulin growth factor-2 (IGF2)
      gene

<400> SEQUENCE: 66
gtgctcgtgt gtgtgctgtg ttcatgygtg tgctgtgtgt tgtgtgtgtg ta          52

<210> SEQ ID NO 67
<211> LENGTH: 52
<212> TYPE: DNA
<213> ORGANISM: Artificial Sequence
<220> FEATURE:
<223> OTHER INFORMATION: known single nucleotide polymorphism (SNP)
      rs56154171 in human insulin growth factor-2 (IGF2)
      gene

<400> SEQUENCE: 67
tgtgctgtgc tcgtgtgtgt gctgtgytca tgcgtgtgct gtgtgttgtg tg          52

<210> SEQ ID NO 68
<211> LENGTH: 53
<212> TYPE: DNA
<213> ORGANISM: Artificial Sequence
<220> FEATURE:
<223> OTHER INFORMATION: known single nucleotide polymorphism (SNP)
      rs59198946 in human insulin growth factor-2 (IGF2)
      gene
<220> FEATURE:
<221> NAME/KEY: modified_base
<222> LOCATION: (7)...(8)
<223> OTHER INFORMATION: at at positions 7 and 8 may be present or
      absent

<400> SEQUENCE: 68
gtgctgtgcg tttgtgtgtg tgctgtatgc tcgtgtgtgt gctgtgttca tgc         53

<210> SEQ ID NO 69
<211> LENGTH: 52
<212> TYPE: DNA
<213> ORGANISM: Artificial Sequence
<220> FEATURE:
<223> OTHER INFORMATION: known single nucleotide polymorphism (SNP)
      rs61872709 in human insulin growth factor-2 (IGF2)
      gene

<400> SEQUENCE: 69
tctgtgtgct gtgtgtgctg tgcgttygtg tgtgtgctgt gctcgtgtgt gt          52

<210> SEQ ID NO 70
<211> LENGTH: 52
<212> TYPE: DNA
<213> ORGANISM: Artificial Sequence
<220> FEATURE:
<223> OTHER INFORMATION: known single nucleotide polymorphism (SNP)
      rs61872708 in human insulin growth factor-2 (IGF2)
``` gene

<400> SEQUENCE: 70
catctgtgtg ctgtgtgtgc tgtgcgyttg tgtgtgtgct gtgctcgtgt gt    52

<210> SEQ ID NO 71
<211> LENGTH: 52
<212> TYPE: DNA
<213> ORGANISM: Artificial Sequence
<220> FEATURE:
<223> OTHER INFORMATION: known single nucleotide polymorphism (SNP)
    rs61872707 in human insulin growth factor-2 (IGF2)
    gene

<400> SEQUENCE: 71
tgcgtttgtg tgtgtgctgt gtgtgcrtgt gtgtgcgtgt gtgtgccgtg cg    52

<210> SEQ ID NO 72
<211> LENGTH: 52
<212> TYPE: DNA
<213> ORGANISM: Artificial Sequence
<220> FEATURE:
<223> OTHER INFORMATION: known single nucleotide polymorphism (SNP)
    rs61872706 in human insulin growth factor-2 (IGF2)
    gene

<400> SEQUENCE: 72
gtgctgtgcg tttgtgtgtg tgctgtrtgt gcatgtgtgt gcgtgtgtgt gc    52

<210> SEQ ID NO 73
<211> LENGTH: 52
<212> TYPE: DNA
<213> ORGANISM: Artificial Sequence
<220> FEATURE:
<223> OTHER INFORMATION: known single nucleotide polymorphism (SNP)
    rs11042774 in human insulin growth factor-2 (IGF2)
    gene

<400> SEQUENCE: 73
gtgcgtttgt gtgtgctgtg cgtttgygtg tgtgctgtgt gtgcatgtgt gt    52

<210> SEQ ID NO 74
<211> LENGTH: 55
<212> TYPE: DNA
<213> ORGANISM: Artificial Sequence
<220> FEATURE:
<223> OTHER INFORMATION: known single nucleotide polymorphism (SNP)
    rs59630895 in human insulin growth factor-2 (IGF2)
    gene
<220> FEATURE:
<221> NAME/KEY: modified_base
<222> LOCATION: (7)...(10)
<223> OTHER INFORMATION: tgtg at positions 7-10 may be present or absent

<400> SEQUENCE: 74
ttgtgtgtgt gctgtgtgct agtgtgtgtg ctgtgtgtgc atgtgtgtgc gtgtg    55

<210> SEQ ID NO 75
<211> LENGTH: 52
<212> TYPE: DNA
<213> ORGANISM: Artificial Sequence
<220> FEATURE:
<223> OTHER INFORMATION: known single nucleotide polymorphism (SNP)
    rs7111331 in human insulin growth factor-2 (IGF2)
    gene

<400> SEQUENCE: 75
tgctgtgttc gtgtgtgctg tgttcgygtg tgtgtgctgt gtgtgcatgt gt    52

```
<210> SEQ ID NO 76
<211> LENGTH: 52
<212> TYPE: DNA
<213> ORGANISM: Artificial Sequence
<220> FEATURE:
<223> OTHER INFORMATION: known single nucleotide polymorphism (SNP)
      rs11042767 in human insulin growth factor-2 (IGF2)
      gene exon 9

<400> SEQUENCE: 76
acatttcttg gggggtcccc aggagayggg caaagatgat ccctaggtgt gc            52

<210> SEQ ID NO 77
<211> LENGTH: 51
<212> TYPE: DNA
<213> ORGANISM: Artificial Sequence
<220> FEATURE:
<223> OTHER INFORMATION: known single nucleotide polymorphism (SNP)
      rs7129583 in human insulin growth factor-2 (IGF2)
      gene exon 9

<400> SEQUENCE: 77
agtcctcggg ggccgtgcac tgatgygggg agtgtgggaa gtctggcggt t             51

<210> SEQ ID NO 78
<211> LENGTH: 51
<212> TYPE: DNA
<213> ORGANISM: Artificial Sequence
<220> FEATURE:
<223> OTHER INFORMATION: known single nucleotide polymorphism (SNP)
      rs28462050 in human insulin growth factor-2 (IGF2)
      gene exon 9

<400> SEQUENCE: 78 gcattttttcc tttttttttt tttttygttt tttttttacc cctccttagc t            51

<210> SEQ ID NO 79
<211> LENGTH: 53
<212> TYPE: DNA
<213> ORGANISM: Artificial Sequence
<220> FEATURE:
<223> OTHER INFORMATION: known single nucleotide polymorphism (SNP)
      rs28472590 in human insulin growth factor-2 (IGF2)
      gene exon 9
<220> FEATURE:
<221> NAME/KEY: modified_base
<222> LOCATION: (7)...(8)
<223> OTHER INFORMATION: gg at positions 7 and 8 may be present or
      absent

<400> SEQUENCE: 79
tgcccccctg ttacatgggg gggggggtt taatttggtt tctgagcgca taa            53

<210> SEQ ID NO 80
<211> LENGTH: 52
<212> TYPE: DNA
<213> ORGANISM: Artificial Sequence
<220> FEATURE:
<223> OTHER INFORMATION: known single nucleotide polymorphism (SNP)
      rs58312807 in human insulin growth factor-2 (IGF2)
      gene exon 9

<400> SEQUENCE: 80
gagtcctcgg gggccgtgca ctgatgyggg gagtgtggga agtctggcgg tt            52

<210> SEQ ID NO 81
<211> LENGTH: 51
<212> TYPE: DNA
<213> ORGANISM: Artificial Sequence
```

-continued

```
<220> FEATURE:
<223> OTHER INFORMATION: known single nucleotide polymorphism (SNP)
      rs60649995 in human insulin growth factor-2 (IGF2)
      gene exon 9

<400> SEQUENCE: 81
aggctggccg gaggggaagg ggctarcagg tgtgtaaaca gagggttcca t          51

<210> SEQ ID NO 82
<211> LENGTH: 52
<212> TYPE: DNA
<213> ORGANISM: Artificial Sequence
<220> FEATURE:
<223> OTHER INFORMATION: known single nucleotide polymorphism (SNP)
      rs58562468 in human insulin growth factor-2 (IGF2)
      gene exon 9

<400> SEQUENCE: 82
cagggtggcc gccttccgca cacttgrgga accctcccct ctccctcggt ga         52

<210> SEQ ID NO 83
<211> LENGTH: 52
<212> TYPE: DNA
<213> ORGANISM: Artificial Sequence
<220> FEATURE:
<223> OTHER INFORMATION: known single nucleotide polymorphism (SNP)
      rs1065687 in human insulin growth factor-2 (IGF2)
      gene exon 9

<400> SEQUENCE: 83
cgccttccgc acacttgagg aaccctsccc tctccctcgg tgacatcttg cc         52

<210> SEQ ID NO 84
<211> LENGTH: 52
<212> TYPE: DNA
<213> ORGANISM: Artificial Sequence
<220> FEATURE:
<223> OTHER INFORMATION: known single nucleotide polymorphism (SNP)
      rs3208122 in human insulin growth factor-2 (IGF2)
      gene exon 9

<400> SEQUENCE: 84
taagcaacta cgatatctgt atggatmagg ccaaagtccc gctaagattc tc         52

<210> SEQ ID NO 85
<211> LENGTH: 51
<212> TYPE: DNA
<213> ORGANISM: Artificial Sequence
<220> FEATURE:
<223> OTHER INFORMATION: known single nucleotide polymorphism (SNP)
      rs3168310 in human insulin growth factor-2 (IGF2)
      gene exon 9

<400> SEQUENCE: 85
ccaatgtttt catggtctga gccccsctcc tgttcccatc tccactgccc c          51

<210> SEQ ID NO 86
<211> LENGTH: 52
<212> TYPE: DNA
<213> ORGANISM: Artificial Sequence
<220> FEATURE:
<223> OTHER INFORMATION: known single nucleotide polymorphism (SNP)
      rs58527086 in human insulin growth factor-2 (IGF2)
      gene exon 9
<220> FEATURE:
<221> NAME/KEY: modified_base
<222> LOCATION: (7)...(7)
<223> OTHER INFORMATION: t at position 7 may be present or absent

<400> SEQUENCE: 86
```

```
catcgtggct cacgctgcgg gggccgtggg gacaggcgcc aaggaggcca gc          52
```

<210> SEQ ID NO 87
<211> LENGTH: 52
<212> TYPE: DNA
<213> ORGANISM: Artificial Sequence
<220> FEATURE:
<223> OTHER INFORMATION: known single nucleotide polymorphism (SNP)
      rs57156844 in human insulin growth factor-2 (IGF2)
      gene exon 9

<400> SEQUENCE: 87

```
acatttcttg gggggtcccc aggagayggg caaagatgat ccctaggtgt gc          52
```

<210> SEQ ID NO 88
<211> LENGTH: 51
<212> TYPE: DNA
<213> ORGANISM: Artificial Sequence
<220> FEATURE:
<223> OTHER INFORMATION: known single nucleotide polymorphism (SNP)
      rs3802971 in human insulin growth factor-2 (IGF2)
      gene exon 9

<400> SEQUENCE: 88

```
agtcctcggg ggccgtgcac tgatgyggg agtgtgggaa gtctggcggt t            51
```

<210> SEQ ID NO 89
<211> LENGTH: 51
<212> TYPE: DNA
<213> ORGANISM: Artificial Sequence
<220> FEATURE:
<223> OTHER INFORMATION: known single nucleotide polymorphism (SNP)
      rs3180700 in human insulin growth factor-2 (IGF2)
      gene exon 9

<400> SEQUENCE: 89

```
gcatttttcc tttttttttt ttttkgttt ttttttacc cctccttagc t             51
```

<210> SEQ ID NO 90
<211> LENGTH: 53
<212> TYPE: DNA
<213> ORGANISM: Artificial Sequence
<220> FEATURE:
<223> OTHER INFORMATION: known single nucleotide polymorphism (SNP)
      rs57423851 in human insulin growth factor-2 (IGF2)
      gene exon 9
<220> FEATURE:
<221> NAME/KEY: modified_base
<222> LOCATION: (7)...(8)
<223> OTHER INFORMATION: gg at positions 7 and 8 may be present or
      absent

<400> SEQUENCE: 90

```
tgccccctg ttacatgggg ggggggggtt taatttggtt tctgagcgca taa         53
```

<210> SEQ ID NO 91
<211> LENGTH: 52
<212> TYPE: DNA
<213> ORGANISM: Artificial Sequence
<220> FEATURE:
<223> OTHER INFORMATION: known single nucleotide polymorphism (SNP)
      rs35818489 in human insulin growth factor-2 (IGF2)
      gene exon 9

<400> SEQUENCE: 91

```
gagtcctcgg gggccgtgca ctgatgyggg gagtgtggga agtctggcgg tt          52
```

<210> SEQ ID NO 92

```
<211> LENGTH: 51
<212> TYPE: DNA
<213> ORGANISM: Artificial Sequence
<220> FEATURE:
<223> OTHER INFORMATION: known single nucleotide polymorphism (SNP)
      rs11825733 in human insulin growth factor-2 (IGF2)
      gene exon 9

<400> SEQUENCE: 92
aggctggccg gaggggaagg ggctarcagg tgtgtaaaca gagggttcca t            51

<210> SEQ ID NO 93
<211> LENGTH: 52
<212> TYPE: DNA
<213> ORGANISM: Artificial Sequence
<220> FEATURE:
<223> OTHER INFORMATION: known single nucleotide polymorphism (SNP)
      rs11541377 in human insulin growth factor-2 (IGF2)
      gene exon 9

<400> SEQUENCE: 93
cagggtggcc gccttccgca cacttgrgga accctcccct ctccctcggt ga           52

<210> SEQ ID NO 94
<211> LENGTH: 52
<212> TYPE: DNA
<213> ORGANISM: Artificial Sequence
<220> FEATURE:
<223> OTHER INFORMATION: known single nucleotide polymorphism (SNP)
      rs11541375 in human insulin growth factor-2 (IGF2)
      gene exon 9

<400> SEQUENCE: 94
cgccttccgc acacttgagg aaccctsccc tctccctcgg tgacatcttg cc           52

<210> SEQ ID NO 95
<211> LENGTH: 52
<212> TYPE: DNA
<213> ORGANISM: Artificial Sequence
<220> FEATURE:
<223> OTHER INFORMATION: known single nucleotide polymorphism (SNP)
      rs11541373 in human insulin growth factor-2 (IGF2)
      gene exon 9

<400> SEQUENCE: 95
ggtgacatct tgcccgcccc tcagcaycct gccttgtctc caggaggtcc ga           52

<210> SEQ ID NO 96
<211> LENGTH: 51
<212> TYPE: DNA
<213> ORGANISM: Artificial Sequence
<220> FEATURE:
<223> OTHER INFORMATION: known single nucleotide polymorphism (SNP)
      rs11541372 in human insulin growth factor-2 (IGF2)
      gene exon 9

<400> SEQUENCE: 96
cccctcagca ccctgccttg tctccmggag gtccgaagct ctgtgggacc t            51

<210> SEQ ID NO 97
<211> LENGTH: 52
<212> TYPE: DNA
<213> ORGANISM: Artificial Sequence
<220> FEATURE:
<223> OTHER INFORMATION: known single nucleotide polymorphism (SNP)
      rs11541374 in human insulin growth factor-2 (IGF2)
      gene exon 9
```

<210> SEQ ID NO 98
<211> LENGTH: 52
<212> TYPE: DNA
<213> ORGANISM: Artificial Sequence
<220> FEATURE:
<223> OTHER INFORMATION: known single nucleotide polymorphism (SNP)
      rs3189464 in human insulin growth factor-2 (IGF2)
      gene exon 9

<400> SEQUENCE: 98
cctcgccccc acttgtgccc ccagctmagc ccccctgcac gcagcccgac ta           52

<210> SEQ ID NO 99
<211> LENGTH: 51
<212> TYPE: DNA
<213> ORGANISM: Artificial Sequence
<220> FEATURE:
<223> OTHER INFORMATION: known single nucleotide polymorphism (SNP)
      rs61745040 in human insulin growth factor-2 (IGF2)
      gene exon 9

<400> SEQUENCE: 99
cagtcgcaga gggtccctcg gcaagygccc tgtgagtggg ccattcggaa c            51

<210> SEQ ID NO 100
<211> LENGTH: 51
<212> TYPE: DNA
<213> ORGANISM: Artificial Sequence
<220> FEATURE:
<223> OTHER INFORMATION: known single nucleotide polymorphism (SNP)
      rs11564732 in human insulin growth factor-2 (IGF2)
      gene exon 9

<400> SEQUENCE: 100
agtcgcagag ggtccctcgg caagcdccct gtgagtgggc cattcggaac a            51

<210> SEQ ID NO 101
<211> LENGTH: 51
<212> TYPE: DNA
<213> ORGANISM: Artificial Sequence
<220> FEATURE:
<223> OTHER INFORMATION: known single nucleotide polymorphism (SNP)
      rs11541376 in human insulin growth factor-2 (IGF2)
      gene exon 9

<400> SEQUENCE: 101
gcaagcgccc tgtgagtggg ccattyggaa cattggacag aagcccaaag a            51

<210> SEQ ID NO 102
<211> LENGTH: 51
<212> TYPE: DNA
<213> ORGANISM: Artificial Sequence
<220> FEATURE:
<223> OTHER INFORMATION: known single nucleotide polymorphism (SNP)
      rs7873 in human insulin growth factor-2 (IGF2) gene exon 9

<400> SEQUENCE: 102
gtgttcccgg gggcacttgc cgaccrgccc cttgcgtccc caggtttgca g            51

<210> SEQ ID NO 103
<211> LENGTH: 51
<212> TYPE: DNA
<213> ORGANISM: Artificial Sequence
<220> FEATURE:

```
<223> OTHER INFORMATION: known single nucleotide polymorphism (SNP)
      rs61745039 in human insulin growth factor-2 (IGF2)
      gene exon 9

<400> SEQUENCE: 103
gggcacttgc cgaccagccc cttgcdtccc caggtttgca gctctcccct g            51

<210> SEQ ID NO 104
<211> LENGTH: 52
<212> TYPE: DNA
<213> ORGANISM: Artificial Sequence
<220> FEATURE:
<223> OTHER INFORMATION: known single nucleotide polymorphism (SNP)
      rs3177805 in human insulin growth factor-2 (IGF2)
      gene exon 9

<400> SEQUENCE: 104
ttgtctcctc cccgtgtccc caatgtyttc agtgggggc cccctcttgg gt             52

<210> SEQ ID NO 105
<211> LENGTH: 52
<212> TYPE: DNA
<213> ORGANISM: Artificial Sequence
<220> FEATURE:
<223> OTHER INFORMATION: known single nucleotide polymorphism (SNP)
      rs1065715 in human insulin growth factor-2 (IGF2)
      gene exon 9

<400> SEQUENCE: 105
cgtgtcccca atgtcttcag tgggggsccc cctcttgggt ccctcctct gc             52

<210> SEQ ID NO 106
<211> LENGTH: 51
<212> TYPE: DNA
<213> ORGANISM: Artificial Sequence
<220> FEATURE:
<223> OTHER INFORMATION: known single nucleotide polymorphism (SNP)
      rs11541371 in human insulin growth factor-2 (IGF2)
      gene exon 9

<400> SEQUENCE: 106
tgtccccaat gtcttcagtg ggggsccccc tcttgggtcc cctcctctgc c             51

<210> SEQ ID NO 107
<211> LENGTH: 52
<212> TYPE: DNA
<213> ORGANISM: Artificial Sequence
<220> FEATURE:
<223> OTHER INFORMATION: known single nucleotide polymorphism (SNP)
      rs1049926 in human insulin growth factor-2 (IGF2)
      gene exon 9

<400> SEQUENCE: 107
ccaatgtctt cagtgggggg cccctyttg gtccctcc tctgccatca cc               52

<210> SEQ ID NO 108
<211> LENGTH: 51
<212> TYPE: DNA
<213> ORGANISM: Artificial Sequence
<220> FEATURE:
<223> OTHER INFORMATION: known single nucleotide polymorphism (SNP)
      rs3177946 in human insulin growth factor-2 (IGF2)
      gene exon 9

<400> SEQUENCE: 108 ggggcccct cttgggtccc ctcctytgcc atcacctgaa gaccccacg c               51

<210> SEQ ID NO 109
```

```
<211> LENGTH: 52
<212> TYPE: DNA
<213> ORGANISM: Artificial Sequence
<220> FEATURE:
<223> OTHER INFORMATION: known single nucleotide polymorphism (SNP)
      rs1050035 in human insulin growth factor-2 (IGF2)
      gene exon 9

<400> SEQUENCE: 109
gtcacctgtg cctgccgcct cggtccmcct tgcggcccgt gtttgactca ac          52

<210> SEQ ID NO 110
<211> LENGTH: 52
<212> TYPE: DNA
<213> ORGANISM: Artificial Sequence
<220> FEATURE:
<223> OTHER INFORMATION: known single nucleotide polymorphism (SNP)
      rs11541370 in human insulin growth factor-2 (IGF2)
      gene exon 9

<400> SEQUENCE: 110
aatattagcg ttaaaggagc tgagttragt caaacacggg ccgcaaggtg ga          52

<210> SEQ ID NO 111
<211> LENGTH: 51
<212> TYPE: DNA
<213> ORGANISM: Artificial Sequence
<220> FEATURE:
<223> OTHER INFORMATION: known single nucleotide polymorphism (SNP)
      rs2585 in human insulin growth factor-2 (IGF2) gene exon 9
<220> FEATURE:
<221> NAME/KEY: modified_base
<222> LOCATION: (26)...(26)
<223> OTHER INFORMATION: n = g, a, c or t

<400> SEQUENCE: 111
tgcggcccgt gtttgactca actcanctcc tttaacgcta atatttccgg c           51

<210> SEQ ID NO 112
<211> LENGTH: 51
<212> TYPE: DNA
<213> ORGANISM: Artificial Sequence
<220> FEATURE:
<223> OTHER INFORMATION: known single nucleotide polymorphism (SNP)
      rs1050141 in human insulin growth factor-2 (IGF2)
      gene exon 9

<400> SEQUENCE: 112
gggttttgtc tttaaccttg taacgmttgc aatcccaata aagcattaaa a           51

<210> SEQ ID NO 113
<211> LENGTH: 29
<212> TYPE: DNA
<213> ORGANISM: Artificial Sequence
<220> FEATURE:
<223> OTHER INFORMATION: primer for single nucleotide extension assay
      using PCR amplicon of known single nucleotide
      polymorphism (SNP) rs680 in human insulin growth
      factor-2 (IGF2) gene

<400> SEQUENCE: 113
gtccctgaac cagcaaagag aaaagaagg                                    29

<210> SEQ ID NO 114
<211> LENGTH: 84
<212> TYPE: DNA
<213> ORGANISM: Artificial Sequence
<220> FEATURE:
<223> OTHER INFORMATION: PCR amplicon for known single nucleotide
      polymorphism (SNP) rs680 in human insulin growth
```

```
                factor-2 (IGF2) gene

<400> SEQUENCE: 114
tggacttgag tccctgaacc agcaaagaga gaaaagaagg accccagaaa tcacaggtgg      60
gcacgtcgct gctaccgcca tctc                                            84

<210> SEQ ID NO 115
<211> LENGTH: 30
<212> TYPE: DNA
<213> ORGANISM: Artificial Sequence
<220> FEATURE:
<223> OTHER INFORMATION: single nucleotide primer extension for known
      single nucleotide polymorphism (SNP) rs680 in
      human insulin growth factor-2 (IGF2) gene
<220> FEATURE:
<221> NAME/KEY: modified_base
<222> LOCATION: (30)...(30)
<223> OTHER INFORMATION: g modified by dR110 fluorescent dye label

<400> SEQUENCE: 115
gtccctgaac cagcaaagag aaaagaaggg                                      30

<210> SEQ ID NO 116
<211> LENGTH: 30
<212> TYPE: DNA
<213> ORGANISM: Artificial Sequence
<220> FEATURE:
<223> OTHER INFORMATION: single nucleotide primer extension for known
      single nucleotide polymorphism (SNP) rs680 in
      human insulin growth factor-2 (IGF2) gene
<220> FEATURE:
<221> NAME/KEY: modified_base
<222> LOCATION: (30)...(30)
<223> OTHER INFORMATION: a modified by dR6G fluorescent dye label

<400> SEQUENCE: 116
gtccctgaac cagcaaagag aaaagaagga                                      30
```